United States Patent
Kobe et al.

(10) Patent No.: US 11,591,541 B2
(45) Date of Patent: Feb. 28, 2023

(54) POLYMERIC COMPOSITE PARTICLES

(71) Applicant: 3M INNOVATIVE PROPERTIES COMPANY, St. Paul, MN (US)

(72) Inventors: Michael W. Kobe, Lake Elmo, MN (US); Mary M. Caruso Dailey, Maplewood, MN (US); Luke E. Heinzen, Shoreview, MN (US); Hassan Sahouani, Hastings, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 436 days.

(21) Appl. No.: 17/015,121

(22) Filed: Sep. 9, 2020

(65) Prior Publication Data
US 2020/0399559 A1   Dec. 24, 2020

Related U.S. Application Data

(62) Division of application No. 15/558,319, filed as application No. PCT/US2016/020334 on Mar. 2, 2016, now abandoned.
(Continued)

(51) Int. Cl.
*C11B 9/00* (2006.01)
*A61K 8/34* (2006.01)
(Continued)

(52) U.S. Cl.
CPC .......... *C11B 9/0003* (2013.01); *A61K 8/0208* (2013.01); *A61K 8/0279* (2013.01);
(Continued)

(58) Field of Classification Search
CPC .................................................... C11B 9/0003
See application file for complete search history.

(56) References Cited

U.S. PATENT DOCUMENTS

| 4,828,542 A | 5/1989 | Hermann |
| 6,048,908 A | 4/2000 | Kitagawa |

(Continued)

FOREIGN PATENT DOCUMENTS

| EP | 1533415 | 5/2005 |
| EP | 1797946 | 6/2007 |

(Continued)

OTHER PUBLICATIONS

Leonardos, "Odor Threshold Determinations of 53 Odorant Chemicals" Journal of the Air Pollution Control Associate, 1969, vol. 19, No. 2, pp. 91-95.
(Continued)

*Primary Examiner* — Arrie L Reuther
(74) *Attorney, Agent, or Firm* — Adrian L. Pishko

(57) ABSTRACT

Compositions are provided that include a matrix and a polymeric composite particles disposed in the matrix. The polymeric composite particles include a porous polymeric core and a fragrance positioned within the porous polymeric core. Polymeric composite particles are also provided including a porous polymeric core, a fragrance positioned within the porous polymeric core, and a coating layer around the porous polymeric core. Further, a method of determining a minimum temperature of a composition is provided including providing a composition including polymeric composite particles disposed in a matrix, heating the composition, releasing at least a portion of the fragrance as a vapor from the porous polymeric core of the polymeric composite particles at or above the minimum temperature, and detecting at least a portion of the fragrance vapor in a location outside of the matrix.

20 Claims, 8 Drawing Sheets

Related U.S. Application Data

(60) Provisional application No. 62/136,859, filed on Mar. 23, 2015.

(51) Int. Cl.
*A61Q 13/00* (2006.01)
*A61K 8/81* (2006.01)
*A61K 8/11* (2006.01)
*A61K 8/73* (2006.01)
*A61K 8/02* (2006.01)
*A61K 8/85* (2006.01)
*C08J 3/12* (2006.01)
*C08J 9/26* (2006.01)

(52) U.S. Cl.
CPC ............... *A61K 8/11* (2013.01); *A61K 8/345* (2013.01); *A61K 8/73* (2013.01); *A61K 8/8152* (2013.01); *A61K 8/85* (2013.01); *A61Q 13/00* (2013.01); *C08J 3/126* (2013.01); *C08J 9/26* (2013.01); *C11B 9/0034* (2013.01); *C08J 2333/14* (2013.01); *C08J 2335/02* (2013.01)

(56) References Cited

U.S. PATENT DOCUMENTS

| | | |
|---|---|---|
| 7,015,156 B2 | 3/2006 | Maldonado |
| 7,947,644 B2 | 5/2011 | Uitenbroek |
| 9,422,411 B2 | 8/2016 | Sahouani |
| 2007/0225430 A1 | 9/2007 | Masuda |
| 2009/0176098 A1 | 7/2009 | Masuda |
| 2010/0104647 A1 | 4/2010 | Ting |
| 2010/0316845 A1 | 12/2010 | Rule |
| 2011/0123456 A1 | 5/2011 | Pandidt |
| 2014/0044761 A1 | 2/2014 | Lei |

FOREIGN PATENT DOCUMENTS

| | | |
|---|---|---|
| EP | 1947121 | 7/2008 |
| WO | WO 2007-075442 | 7/2007 |
| WO | WO 2007-075508 | 7/2007 |
| WO | WO 2013-077981 | 5/2013 |
| WO | WO 2014-029695 | 2/2014 |
| WO | WO 2014-186328 | 11/2014 |
| WO | WO 2014-186336 | 11/2014 |
| WO | WO 2015-094710 | 6/2015 |
| WO | WO 2015-095100 | 6/2015 |
| WO | WO 2016-053830 | 4/2016 |

OTHER PUBLICATIONS

Rouette, "Deodorant" and "Fragrant finishes," Encyclopedia of Textile Finishing, Woodhead Publishing, pp. 22, 126-127. (Year: 2001).

International Search report for PCT international Application No. PCT/US2016/020334 dated Jun. 24, 2016, 5 pages.

37.5 μm 20.0 μm

POLYMERIC COMPOSITE PARTICLES

CROSS REFERENCE TO RELATED APPLICATIONS

This application is a divisional application of U.S. application Ser. No. 15/558,319, filed Sep. 14, 2017, which is a national stage filing under 35 U.S.C. 371 of PCT/US2016/020334, filed Mar. 2, 2016, which claims the benefit of U.S. Application No. 62/136,859, filed Mar. 23, 2015, the disclosures of which is incorporated by reference in their entirety herein.

FIELD

Polymeric composite particles and compositions including the polymeric composite particles are provided, for instance for use in thermally-triggerable applications.

BACKGROUND

Various polymeric particles have been prepared. Some of these have been used, for example, as ion exchange resins or other chromatographic resins. Others have been used, for example, to adsorb and/or deliver different active agents. Such particles are described, for example, in U.S. Patent Application 2010/0104647 (Ting), U.S. Patent Application Publication 2011/0123456 (Pandidt et al.), U.S. Pat. No. 6,048,908 (Kitagawa), and Patent Application Publications WO 2013/077981 (Sahouani), WO 2007/075508 (Rasmussen et al.), and WO 2007/075442 (Ramussen et al.).

SUMMARY

Polymeric composite particles and compositions containing polymeric composite particles are provided, as are methods of determining a minimum temperature of a composition. More particularly, the polymeric composite particles and compositions can be used for controlled fragrance release and non-visual temperature indicators for thermal treatment applications.

In a first aspect, a composition is provided. The composition includes a matrix and a plurality of polymeric composite particles disposed in the matrix. The polymeric composite particles include a porous polymeric core and a fragrance positioned within the porous polymeric core. In many embodiments, the polymeric composite particles further include a coating layer around the porous polymeric core.

In a second aspect, a polymeric composite particle is provided. The polymeric composite particle includes a) a porous polymeric core; b) a fragrance positioned within the porous polymeric core; and c) a coating layer around the porous polymeric core. The coating layer includes a thermoplastic polymer, a wax, or a mixture thereof. The fragrance is not covalently bonded to the porous polymeric core. The porous polymeric core comprises a polymerized product of a reaction mixture including a) a first phase and b) a second phase dispersed in the first phase. The first phase includes 1) water and a polysaccharide dissolved in the water and/or 2) a surfactant and a compound of Formula (I).

$$HO(-CH_2-CH(OH)-CH_2-O)_n-H \qquad (I)$$

In Formula (I), n is an integer equal to at least 1. A volume of the first phase is greater than a volume of the second phase. The second phase includes 1) a monomer composition comprising a monomer of Formula (II) and 2) a poly (propylene glycol) having a weight average molecular weight of at least 500 grams/mole. The poly(propylene glycol) is removed from the polymerized product to provide the porous polymeric core.

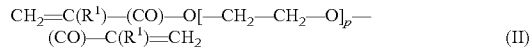

$$CH_2=C(R^1)-(CO)-O[-CH_2-CH_2-O]_p- \\ (CO)-C(R^1)=CH_2 \qquad (II)$$

In Formula (II), p is an integer equal to at least 1 and $R^1$ is a hydrogen or alkyl.

In a third aspect, a method of determining a minimum temperature of a composition is provided. The method includes a) providing a composition comprising a plurality of polymeric composite particles disposed in a matrix, wherein the polymeric composite particles include a porous polymeric core and a fragrance positioned within the porous polymeric core. The method further includes b) heating the composition; c) releasing at least a portion of the fragrance as a vapor from the porous polymeric core of the polymeric composite particles at or above the minimum temperature; and d) detecting at least a portion of the fragrance vapor in a location outside of the matrix.

Figure 1:
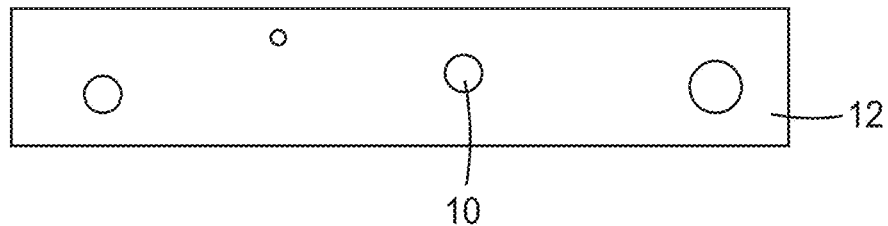
FIG. 1 is a schematic of an exemplary composition according to the disclosure.

While the above-identified drawings, which may not be drawn to scale, set forth various embodiments of the present disclosure, other embodiments are also contemplated, as noted in the Detailed Description. In all cases, this disclosure describes the presently disclosed disclosure by way of

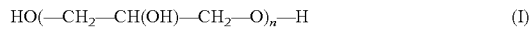

representation of exemplary embodiments and not by express limitations. It should be understood that numerous other modifications and embodiments can be devised by those skilled in the art, which fall within the scope and spirit of this disclosure

DETAILED DESCRIPTION

Various exemplary embodiments of the disclosure will now be described, with particular reference to the Examples and the Figures. Exemplary embodiments of the disclosure may take on various modifications and alterations without departing from the spirit and scope of the disclosure. Accordingly, it is to be understood that the embodiments of the disclosure are not to be limited to the following described exemplary embodiments, but is to be controlled by the limitations set forth in the claims and any equivalents thereof.

Various applications benefit from releasing a fragrance at a predetermined temperature, for instance materials designed to impart a fragrance to other materials (e.g., dryer sheets or deodorants). It would also be useful to provide a non-visual method of determining when a composition has reached a particular minimum temperature (e.g., electrical components or heat-debondable adhesives that are located out of view). It has been discovered that polymeric composite particles can be included in compositions and a fragrance released from the polymeric composite particles when the particles in the composition reach a minimum temperature.

The porous polymeric particles have pores on their outer surfaces and typically have hollow interiors. The terms "porous polymeric particle" and "polymeric particle" are used interchangeably. Following synthesis, the particles are filled with a solution-based fragrance, then typically a temperature-responsive shell is applied to the exterior surfaces of the loaded particles to yield a controlled release polymeric composite particle. The coating allows the interior contents of the particles to remain inside the particle until a certain temperature has been reached or until exposed to certain solvents. Alternatively, a hydrophobic fragrance can be loaded into hydrophilic particles and the opposite polarities of the functional groups of the fragrance and particle wall will retain the fragrance until release is triggered. The release of fragrance from polymeric composite particles is triggered by heat and/or exposure to certain solvents, including water, to release their contents. Once triggered, the coating (if present) will soften, allowing for the release of the interior contents into the surrounding matrix environment.

As used throughout this specification and the appended embodiments, the words "suitable" and "preferably" refer to embodiments of the disclosure that may afford certain benefits under certain circumstances. Other embodiments may also be suitable, however, under the same or other circumstances. Furthermore, the recitation of one or more suitable embodiments does not imply that other embodiments are not useful, and is not intended to exclude other embodiments from the scope of the disclosure.

As used throughout this specification and the appended embodiments, the term "comprises" and variations thereof do not have a limiting meaning where these terms appear in the description and claims.

As used throughout this specification and the appended embodiments, the recitation of numerical ranges by endpoints includes all numbers subsumed within that range (e.g. 1 to 5 includes 1, 1.5, 2, 2.75, 3, 3.8, 4, and 5).

Unless otherwise indicated throughout this specification and the appended embodiments, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

For the following Glossary of defined terms, these definitions shall be applied for the entire application, including the claims:

Glossary

The term "a", "an", and "the" are used interchangeably with "at least one" to mean one or more of the elements being described.

The term "and/or" means either or both. For example "A and/or B" means only A, only B, or both A and B.

The term "blind location" refers to a position that is not visible, such as behind a structural component or within a composition that is not transparent.

The term "coating layer" refers to a material that is disposed on an exterior surface of a polymeric composite particle. Preferably, a coating layer covers the entire exterior surface of the polymeric composite particle.

The term "fragrance" refers to a compound that has a specific minimum vapor pressure and an odorous vapor, in which the odor is distinguishable from the ambient atmosphere.

The term "heat-debondable adhesive" refers to an adhesive that shows initial adhesion controlled by the pressure of application and a decrease of the adhesion level after the application of heat.

The term "hydrophilic" refers to monomers or particles having polar regions.

The term "hydrophobic" refers to monomers or particles having non-polar regions.

The term "matrix" refers to a medium on which and/or in which a material (e.g., polymeric composite particles) may be disposed. A matrix includes for example and without limitation, a film, a nonwoven matrix, a woven matrix, a foam, a multilayer construction, a suspension, and a gel.

The term "monomer composition" refers to that portion of a polymerizable composition that includes the monomers and only the monomers. More specifically, the monomer composition includes at least the first monomer of Formula (II).

The terms "polymer" and "polymeric material" are used interchangeably and refer to materials formed by reacting one or more monomers. The terms include homopolymers, copolymers, terpolymers, or the like. Likewise, the terms "polymerize" and "polymerizing" refer to the process of making a polymeric material that can be a homopolymer, copolymer, terpolymer, or the like.

The term "reaction mixture" includes, for example, the monomer composition, the poly(propylene glycol), any other components such as those included in the first phase, and the second phase described below. Some of the components in the reaction mixture may not undergo a chemical reaction but can influence the chemical reaction and the resulting polymeric material.

The term "substrate" refers to any material comprising at least one surface on which a material may be disposed. Exemplary substrates include for instance and without limitation tape backings, release liners, and structural materials such as metal, plastic, glass, concrete, and wood.

The term "vapor" refers to both a gas and a suspension of fine droplets of liquid in a gas (e.g., an aerosol).

In a first aspect, a composition is provided. The composition includes a matrix and a plurality of polymeric composite particles disposed in the matrix. The polymeric composite particles include a porous polymeric core and a fragrance positioned within the porous polymeric core. In many embodiments, the polymeric composite particles further include a coating layer around the porous polymer core.

Referring to FIG. 1, a cross-sectional schematic of a composition 100 is shown. The composition 100 includes polymeric composite particles 10 disposed in a matrix 12. A matrix refers to any material that can contain the polymeric composite particles. Exemplary matrices include for instance and without limitation, a film, a nonwoven matrix, a woven matrix, a foam, a multilayer construction, a suspension, a gel, or a combination thereof. In certain embodiments, the matrix comprises a polymeric material. In some embodiments, the matrix comprises an adhesive, such as a heat-debondable adhesive. The term "heat-debondable adhesive" refers to an adhesive that shows initial adhesion controlled by the pressure of application and a decrease of the adhesion level after the application of heat. The decrease in adhesion level remains after the adhesive article has cooled.

Figure 2:
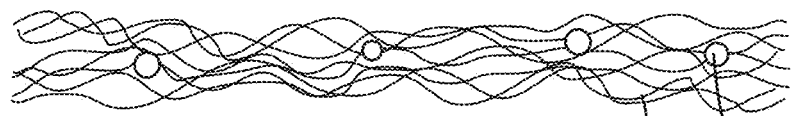
FIG. 2 is a schematic of another exemplary composition according to the disclosure.

Referring to FIG. 2, a cross-sectional schematic of a composition 200 is shown. The composition 200 includes polymeric composite particles 20 disposed in a nonwoven matrix 22. Suitable nonwoven matrices include for example and without limitation, a felt, a spunbond web, a meltblown web, and a wetlaid matrix (e.g., paper). In certain embodiments, the matrix comprises a woven matrix (not shown). Suitable woven matrices include for example and without limitation, a fabric, a scrim, or a net.

Figure 3:
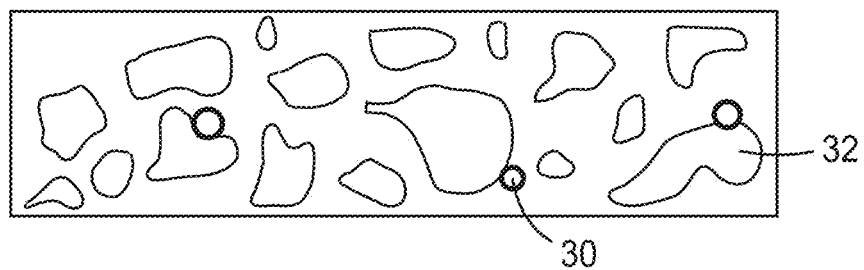
FIG. 3 is a schematic of a further exemplary composition according to the disclosure.

Referring to FIG. 3, a cross-sectional schematic of a composition 300 is shown. The composition 300 includes polymeric composite particles 30 disposed in a foam matrix 32. Suitable foam matrices include for example and without limitation, an open cell foam, a closed cell foam, an aerosolized foam, an aerogel, or a combination thereof. Exemplary specific matrices include natural sponges, polyurethane foams, carboxylated butadiene-sytrene rubber foams, polyester foams, polyacrylate foams, polyether foams, and polyolefin foams.

Figure 4:
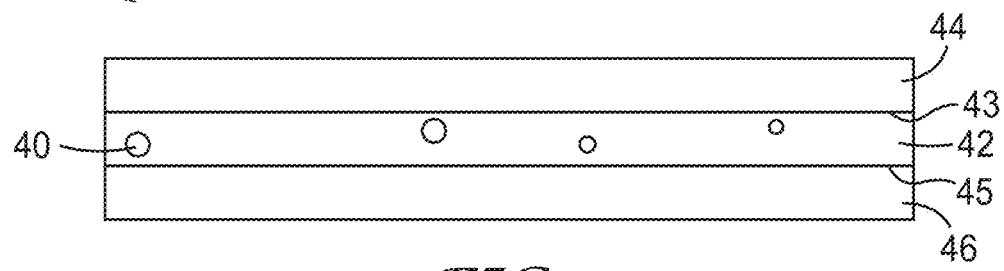
FIG. 4 is a schematic of a still further exemplary composition according to the disclosure.

Referring to FIG. 4, a cross-sectional schematic of a composition 400 is shown. The composition 400 includes polymeric composite particles 40 disposed in an adhesive matrix 42. The adhesive matrix 42 is part of a multilayer construction. More particularly, the adhesive matrix 42 is disposed between a major surface 43 of a first substrate 44 and a major surface 45 of a second substrate 46. In certain embodiments, the polymeric composite particles are not visible from an exterior of the composition. For instance, when one or more of the first substrate 44 and the second substrate 46 are opaque, the adhesive matrix 42 and the polymeric composite particles 40 disposed therein will typically not be viewable from outside of the composition 400. Such opaque substrates include for example and without limitation, metal, colored plastic, woven material, nonwoven material, foam, wood, concrete, glass, ceramic, and combinations thereof. For embodiments including a heat-debondable adhesive as the adhesive matrix, it is useful to have an indication of when the adhesive has been heated sufficiently to debond the adhesive.

Figure 5:
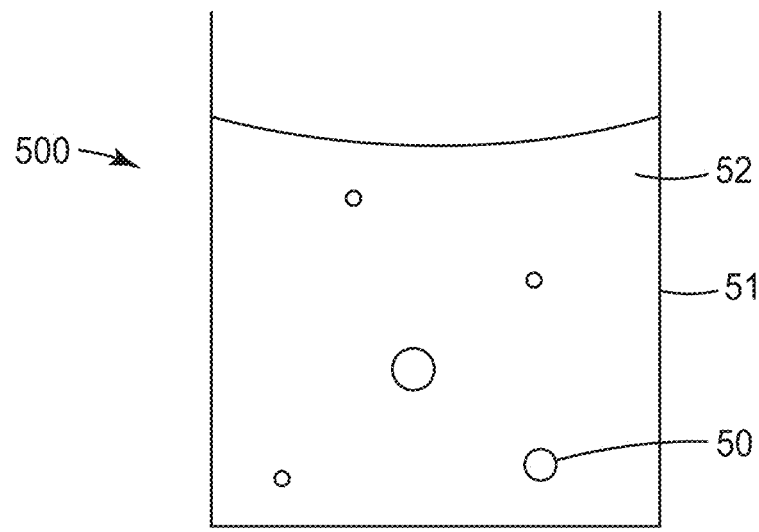
FIG. 5 is a schematic of yet another exemplary composition according to the disclosure.

Referring to FIG. 5, a cross-sectional schematic of a composition 500 is shown. The composition 500 includes polymeric composite particles 50 disposed in a suspension 52. In the illustrated embodiment, the suspension 52 is located in a container 51. Suitable suspensions 52 include for example and without limitation, a lotion, a dispersion, or other emulsions, such as a shampoo or reactants for a chemical reaction.

Figure 6:
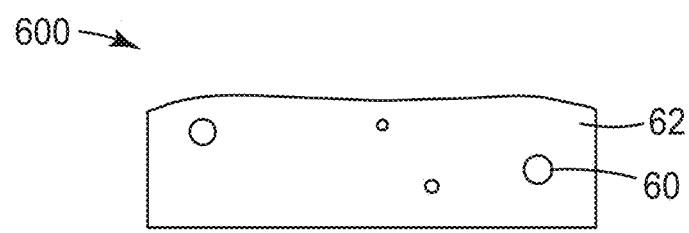
FIG. 6 is a schematic of an additional exemplary composition according to the disclosure.

Referring to FIG. 6, a cross-sectional schematic of a composition 600 is shown. The composition 600 includes polymeric composite particles 60 disposed in a gel 62. Suitable gels 62 include for example and without limitation, a gelatin, a hydrogel, a silicone gel, an organogel, hydroxyethyl cellulose, carboxymethyl cellulose, polyacrylamide, locust bean gum, and algin.

In many embodiments, the fragrance comprises a water insoluble fragrance. By "water insoluble" it is meant that a material has a water solubility of less than one part of material per million parts of water (i.e., 1 ppm). In certain embodiments, however, the fragrance comprises a water soluble fragrance. The fragrance has a vapor pressure that results in at least a portion of the fragrance vaporizing into the surrounding environment such that its presence can be detected, either by a living being that smells the scent of the fragrance, or by a sensor that detects the fragrance molecule. As noted above, the term "fragrance" as used herein comprises a compound that has a specific minimum vapor pressure and an odorous vapor, in which the odor is distinguishable from the ambient atmosphere. Preferably, the fragrance has a vapor pressure at 25 degrees Celsius of at least 0.05 millimeters of mercury (mmHg) (6.67 pascals (Pa)), or at least 0.075 mmHg (1.00 Pa), or at least 0.1 mmHg (13.33 Pa), or at least 0.25 mmHg (33.33 Pa), or at least 0.5 mmHg (66.67 Pa). At higher temperatures, the vapor pressure is concomitantly higher.

Suitable fragrance compounds include for example and without limitation, esters, linear terpenes, cyclic terpenes, aromatics, amines, alcohols, aldehydes, ketones, lactones, and thiols. Suitable esters include for example and without limitation, ethyl methylphenylglycidate, fructone, geranyl acetate, hexyl acetate, methyl formate, methyl acetate, methyl propionate, methyl butyrate, ethyl acetate, ethyl butyrate, isoamyl acetate, pentyl butyrate, pentyl pentanoate, octyl acetate, benzyl acetate, and methyl anthranilate. Suitable linear terpenes include for example and without limitation, myrcene, geraniol, nerol, citral, citronellal, citronellol, linalool, and nerolidol. Suitable cyclic terpenes include for example and without limitation, limonene, camphor, menthol, carvone, terpineol, alpha-ionone, and thujone. Suitable aromatics include for example and without limitation, benzaldehyde, eugenol, cinnamaldehyde, ethyl maltol, vanillin, anisole, anethole, estragole, and thymol. Suitable amines include for example and without limitation, trimethylamine, putrescine, cadaverine, pyridine, indole, and skatole. Suitable alcohols include for example and without limitation, furaneol, 1-hexanol, cis-3-hexen-1-ol, and menthol. Suitable aldehydes include for example and without limitation, acetaldehyde, hexanal, cis-3-hexenal, furfural, hexyl cinnamaldehyde, isovaleraldehyde, anisic aldehyde, and cuminaldehyde. Suitable ketones include for example and without limitation, cyclopentadecanone, dihydrojasmone, oct-1-en-3-one, 2-acetyl-1-pyrroline, and 6-acetyl-2,3,4,5-tetrahydropyridine. Suitable lactones include for example and without limitation, gamma-decalactone, gamma-nonalactone, delta-octalactone, jasmine lactone, massoia lactone, wine lactone, and sotolon. Suitable thiols include for example and without limitation, allyl thiol, (methylthio)methanethiol, ethanethiol, 2-methyl-2-propanethiol, butane-1-thiol, grapefruit mercaptan, methanethiol, furan-2-ylmethanethiol, and benzyl mercaptan. Suitable additional fragrance compounds include for example and without limitation, N,N-diethyl-meta-toluamide (DEET), methylphosphine, dimethylphosphine, phosphine, zinc phosphide, diacetyl, acetoin, nerolin, tetrahydrothiophene, 2,4,6-trichloroanisole, and substituted pyrazines.

Figure 7:
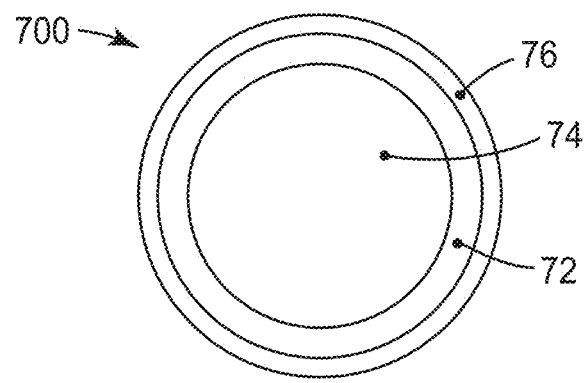
FIG. 7 is a schematic of an exemplary polymeric composite particle according to the disclosure.

In most embodiments, the polymeric composite particles further comprise a coating layer around the porous polymer core, to assist in retaining the fragrance in the polymeric composite particles. Referring to FIG. 7, a cross-sectional schematic of a polymeric composite particle 700 is shown. The polymeric composite particle 700 comprises a porous polymer core 72, a fragrance 74 positioned within the porous polymeric core 72, and an optional coating layer 76 around the porous polymer core 72. In certain embodiments, the polymeric composite particle has a core-shell configuration with the core being the porous polymeric particle and the shell being the coating layer. The coating layer typically comprises a thermoplastic polymer, a wax, or a mixture thereof. Suitable coating layers include for example and without limitation, a silicone-based thermoplastic polymer, a (meth)acrylate-based thermoplastic polymer, an olefin-based thermoplastic polymer, a styrene-based thermoplastic polymer, a phenoxy-based resin, polyvinyl pyrrolidone, animal wax, vegetable wax, petroleum wax, hydrogenated vegetable oil, and combinations thereof. It has been found that a linear thermoplastic polymer, such as high density polyethylene, provides a particularly useful coating layer. Without wishing to be bound by theory, it is believed that due to the close packing of the linear polymers, coating layers comprising linear thermoplastic polymers minimize the diffusion of a fragrance from within a porous polymeric core better than coating layers comprising polymers that are not linear, e.g., branched polymers.

The thickness of the optional coating layer is not particularly limited. A minimum thickness is preferably determined by the least amount of coating that minimizes the diffusion of a fragrance from within a porous polymeric core to be below the threshold perception of a living being, such as described in the article "Odor Threshold Determinations of 53 Odorant Chemicals" (Gregory Leonardos, David Kendall, & Nancy Barnard (1969) Journal of the Air Pollution Control Associate, 19:2, pp. 91-95). The coating layer usually has a thickness of at least 0.1 micrometers, or at least 0.2 micrometers, or at least 0.3 micrometers, or at least 0.5 micrometers, or at least 1 micrometer, or at least 2 micrometers. A maximum thickness is preferably determined by the greatest amount of coating that softens or dissolves when triggered by heat or solvent, respectively, to release fragrance vapor at a specific temperature or solvent contact. The coating layer usually has a thickness of up to 5 micrometers, or up to 4 micrometers, or up to 3 micrometers, or up to 2 micrometers, or up to 1.5 micrometers, or at least 0.75 micrometers. In certain embodiments, the coating layer has a thickness in a range of 0.1 micrometers to 5 micrometers, or 0.1 micrometers to 3 micrometers, or 0.5 micrometers to 2 micrometers.

The amount of porous polymeric particles included in compositions according to the disclosure (e.g., polymeric composite particles disposed in a matrix) is not particularly limited. Typically, the polymeric composite particles are present in the matrix in an amount of at least 0.05% by weight of the total composition, or at least 0.075% by weight, or at least 0.1% by weight, or at least 0.25% by weight, or at least 0.5% by weight, or at least 1% by weight, or at least 2% by weight of the total composition. The polymeric composite particles are usually present in the matrix in an amount of up to 5% by weight of the total composition, or up to 4% by weight, or up to 3% by weight, or up to 2% by weight, or up to 1.5% by weight, or up to 0.75% by weight of the total composition. In certain embodiments, the polymeric composite particles are present in the matrix in an amount of between 0.05% and 5% by weight of the total composition, or between 0.1% and 3% by weight of the total composition. The lower practical limit of polymeric composite particles in the composition can be determined by providing measurable fragrance vapor from the polymeric composite particles upon triggering release of fragrance vapor via elevated temperature or solvent contact. The upper practical limit of porous polymeric particles in the composition can be determined by cost considerations or a measurable fragrance vapor diffusion from the composition prior to deliberately triggering release of the fragrance vapor via elevated temperature or solvent contact. In most embodiments, the thickness of the compositions according to the disclosure is greater than the average diameter of the polymeric composite particles, and is preferably greater than the diameter of the largest polymeric composite particles.

In a second aspect, a polymeric composite particle is provided. The polymeric composite particle includes a) a porous polymeric core; b) a fragrance positioned within the porous polymeric core; and c) a coating layer around the porous polymeric core. The coating layer includes a thermoplastic polymer, a wax, or a mixture thereof. The fragrance is not covalently bonded to the porous polymeric core. The porous polymeric core comprises a polymerized product of a reaction mixture comprising:
  i) a first phase comprising either
  1) water and a polysaccharide dissolved in the water; or
  2) a surfactant and a compound of Formula (I)

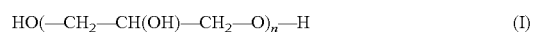

wherein n is an integer equal to at least 1, or a mixture thereof; and
  ii) a second phase dispersed in the first phase, wherein a volume of the first phase is greater than a volume of the second phase and wherein the second phase comprises
  1) a first monomer composition comprising a monomer of Formula (II)

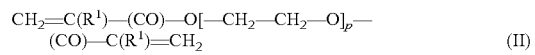

wherein
    p is an integer equal to at least 1;
    $R^1$ is hydrogen or alkyl; and
  2) a poly(propylene glycol) having a weight average molecular weight of at least 500 grams/mole,
  wherein the poly(propylene glycol) is removed from the polymerized product to provide the porous polymeric core.

The variable p in Formula (II) is an integer no greater than 30, no greater than 20, no greater than 16, no greater than 12, or no greater than 10. The number average molecular weight of the ethylene oxide portion of the monomer (i.e., the group —[$CH_2CH_2$—O]$_p$—) is often no greater than 1200 grams/mole, no greater than 1000 grams/mole, no greater than 800 grams/mole, no greater than 1000 grams/mole, no greater than 600 grams/mole, no greater than 400 grams/mole, no greater than 200 grams/mole, or no greater than 100 grams/mole. The group $R^1$ in Formula (I) is hydrogen or methyl.

Suitable first monomers of Formula (II) are commercially available from Sartomer (Exton, Pa., USA) under the trade designation SR206 for ethylene glycol dimethacrylate, SR231 for diethylene glycol dimethacrylate, SR205 for triethylene glycol dimethacrylate, SR210 and SR210A for polyethylene glycol dimethacrylate, SR259 for polyethylene glycol (200) diacrylate, SR603 and SR344 for polyethylene glycol (400) di(meth)acrylate, SR252 and SR610 for polyethylene glycol (600) di(meth)acrylate, and SR740 for polyethylene glycol (1000) dimethacrylate.

The reaction mixture used to form the porous polymeric particles also includes a poly(propylene glycol) having a weight average molecular weight of at least 500 grams/mole. The polypropylene glycol functions as a porogen that gets partially entrained within the polymerized product as it forms from the monomer composition. Because the polypropylene glycol has no polymerizable group, this material can be removed after formation of the polymerized product. Pores (i.e., void volume or free volume) are created when the previously entrained polypropylene glycol is removed. The polymeric particles resulting from the removal of the entrained polypropylene glycol are porous. In certain embodiments, at least some of these porous polymeric particles can have hollow centers, and thus be in the form of hollow beads. The presence of pores or the presence of both pores and hollow centers make the polymeric particles well suited for absorbing and wicking fluids, as well as holding active agents.

Any suitable molecular weight of poly(propylene glycol) can be used as the porogen. The molecular weight can affect the size of the pores that are formed in the polymeric particles. That is, the pore size tends to increase with the molecular weight of the poly(propylene glycol). The weight average molecular weight is often at least 500 grams/mole, at least 800 grams/mole, or at least 1000 grams/mole. The weight average molecular weight of the poly(propylene glycol) can be up to 10,000 gram/mole or greater. For ease of use, a poly(propylene glycol) that is a liquid at room temperature is often selected. Poly(propylene glycol) having a weight average molecular weight up to about 4000 grams/mole or 5000 grams/mole tends to be a liquid at room temperature. Poly(propylene glycol) that is not a liquid at room temperature can be used if it is initially dissolved in a suitable organic solvent such as an alcohol (for example, ethanol, n-propanol, or iso-propanol). The weight average molecular weight of the poly(propylene glycol) is often in a range of 500 to 10,000 grams/mole, in a range of 1000 to 10,000 grams/mole, in a range of 1000 to 8000 grams/mole, in a range of 1000 to 5000 grams/mole, in a range of 1000 to 4000 grams/mole.

In many embodiments, the reaction mixture used to form the porous polymeric particles includes (a) a first phase and (b) a second phase dispersed in the first phase, wherein a volume of the first phase is greater than a volume of the second phase. The first phase contains (i) a compound of Formula (I)

$$HO[-CH_2-CH(OH)-CH_2-O]_n-H \qquad (I)$$

where the variable n is an integer equal to at least 1, and (ii) a nonionic surfactant. The second phase contains (i) a monomer composition comprising the monomer of Formula (I) as described above and (ii) a poly(propylene glycol) having a weight average molecular weight of at least 500 grams/mole. The second phase of the reaction mixture is dispersed in the first phase of the reaction mixture and the volume of the first phase is greater than the volume of the second phase. That is, the first phase can be considered to be the continuous phase and the second phase can be considered to be the dispersed phase within the continuous phase. The first phase provides a non-polymerizable medium for suspending the second phase as droplets within the reaction mixture. The second phase droplets include i) a monomer composition that can undergo polymerization and ii) a porogen, which is poly(propylene glycol) having a weight average molecular weight of at least 500 grams/mole. The monomer of Formula (II) in the second phase is typically not miscible with the first phase.

The first phase of the reaction mixture includes (i) the compound of Formula (I) and (ii) a nonionic surfactant. The first phase is typically formulated to provide a suitable viscosity and volume for dispersion of the second phase as droplets within the first phase. If the viscosity of the first phase is too high, it can be difficult to provide the requisite shear to disperse the second phase. If the viscosity is too low, however, it can be difficult to suspend the second phase and/or to form polymeric particles that are relatively uniform and well separated from each other.

Suitable compounds of Formula (I) typically have a value of n that is in a range of 1 to 20, in a range of 1 to 16, in a range of 1 to 12, in a range of 1 to 10, in a range of 1 to 6, or in a range of 1 to 4. In many embodiments, the compound of Formula (I) is glycerol where the variable n is equal to 1. Other example compounds of Formula (I) are diglycerol (n is equal to 2), polyglycerol-3 (n is equal to 3), polyglycerol-4 (n is equal to 4), or polyglycerol-6 (n is equal to 6). The polyglycerols, which can be referred to as polyglycerins, are often a mixture of materials with varying molecular weight (i.e., materials with different values for n). Polyglycerols, diglycerol, and glycerol are commercially available, for example, from Solvay Chemical (Brussels, Belgium) and Wilshire Technologies (Princeton, N.J., USA).

In addition to the compound of Formula (I), the first phase includes a nonionic surfactant. The nonionic surfactant increases the porosity on the surface of the final polymeric particles. The first phase is typically free or substantially free of an ionic surfactant that could interfere with the polymerization reaction of the monomers within the second phase. As used herein with reference to the ionic surfactant, the term "substantially free" means that no ionic surfactant is purposefully added to the first phase but may be present as a trace impurity in one of the other components in the first phase. Any impurity is typically present in an amount no greater than 0.5 weight percent, no greater than 0.1 weight percent, or no greater than 0.05 weight percent, or no greater than 0.01 weight percent based on a total weight of the first phase.

Any suitable nonionic surfactant can be used in the first phase. The nonionic surfactant often has hydroxyl group or ether linkages (for example, $-CH_2-O-CH_2-$) in one portion of the molecule that can hydrogen bond with other components of the reaction mixture. Suitable nonionic surfactants include, but are not limited to, alkyl glucosides, alkyl glucamides, alkyl polyglucosides, polyethylene glycol alkyl ethers, block copolymers of polyethylene glycol and polypropylene glycol, and polysorbates. Examples of suitable alkyl glucosides include, but are not limited to, octyl glucoside (also referred to as octyl-beta-D-glucopyranoside) and decyl glucoside (also referred to as decyl-beta-D-glucopyranoside). Examples of suitable alkyl glucamides include, but are not limited to, octanoyl-N-methylglucamide, nonanoyl-N-methylglucamide, and decanoyl-N-methylglucamide. These surfactants can be obtained, for example, from Sigma Aldrich (St. Louis, Mo., USA) or Spectrum Chemicals (New Brunswick, N.J., USA). Examples of suitable alkyl polyglucosides include, but are not limited to, those commercially available from Cognis Corporation (Monheim, Germany) under the trade designation APG (for example, APG 325) and those commercially available from Dow Chemical (Midland, Mich., USA) under the trade designation TRITON (for example, TRITON BG-10 and TRITON CG-110). Examples of polyethylene glycol alkyl ethers include, but are not limited to, those commercially available under the trade designation BRIJ (for example, BRIJ 58 and BRIJ 98) from Sigma Aldrich (St. Louis, Mo., USA). Examples of block copolymers of polyethylene glycol and polypropylene glycol include, but are not limited to, those commercially available under the trade designation PLURONIC from BASF (Florham Park, N.J., USA). Examples of polysorbates include, but are not limited to, those commercially available under the trade designation TWEEN from ICI American, Inc. (Wilmington, Del., USA).

The surfactant can be present in the first phase in any suitable amount. Often, the surfactant is present in an amount equal to at least 0.5 weight percent, at least 1 weight percent, or at least 2 weight percent based on a total weight of the first phase. The surfactant can be present in an amount up to 15 weight percent, up to 12 weight percent, or up to 10 weight percent based on a total weight of the first phase. For example, the surfactant is often present in the first phase in an amount in a range of 0.5 to 15 weight percent, in a range of 1 to 12 weight percent, in a range of 0.5 to 10 weight percent, or in a range of 1 to 10 weight percent based on the total weight of the first phase.

Optionally, water or an organic solvent that is miscible with the compound of Formula (I) can be present in the first reaction mixture. Suitable organic solvents include, for example, an alcohol such as methanol, ethanol, n-propanol, or isopropanol. The amount of any optional water or organic solvent is selected so that the desired viscosity of the first phase can be achieved. The amounts of the optional water or organic solvent is often no greater than 10 weight percent, no greater than 5 weight percent, or no greater than 1 weight percent based on the total weight of the first phase. If higher amounts of water are included, the porosity may decrease. In some embodiments, the first phase is free or substantially free of the optional water or organic solvent. As used herein with reference to the optional water or organic solvent, the term "substantially free" means that water or organic solvent is not purposely added to the first phase but may be present as an impurity in one of the other components in the first phase. For example, the amount of the optional water or organic solvent is less than 1 percent, less than 0.5 weight percent, or less than 0.1 weight percent based on a total weight of the first phase.

The reaction mixture includes a second phase dispersed in the first phase. The second phase includes both i) a monomer composition and ii) a poly(propylene glycol) having a weight average molecular weight of at least 500 grams/mole. The monomer composition is polymerized in the second phase to from the polymeric particles. The polypropylene glycol functions as a porogen that gets partially entrained within the polymerized product as it is formed from the monomer composition.

The volume of the first phase is greater than the volume of the second phase. The volume of the first phase is sufficiently large compared to the volume of the second phase so that the second phase can be dispersed in the form of droplets within the first phase. Within each droplet, the monomer composition is polymerized to form a polymerized product. To form particles from the second phase, the volume ratio of the first phase to the second phase is typically at least 2:1. As the volume ratio increases (for example, when the ratio is at least 3:1, at least 4:1, or at least 5:1), beads can be formed that have a relatively uniform size and shape. If the volume ratio is too large, however, the reaction efficiency is diminished (i.e., a smaller amount of polymeric particles is produced). The volume ratio is generally no greater than 25:1, no greater than 20:1, no greater than 15:1, or no greater than 10:1.

In some embodiments, the first monomer of Formula (II) as described above is the only monomer in the monomer composition of the second phase. In other embodiments, the first monomer of Formula (II) can be used in combination with at least one second monomer. The second monomer has a single free radically polymerizable group such as an ethylenically unsaturated group, which is often a (meth) acryloyl group of formula $H_2C=CR^1-(CO)-$ where $R^1$ is hydrogen or methyl. Suitable second monomers are not miscible with the first phase but can be miscible or not miscible with the first monomer of Formula (II). The second monomer is often added to alter the hydrophobicity or hydrophilicity of the porous polymeric material. The addition of these monomers can, however, diminish the porosity of the polymeric particles and/or increase the size of the polymeric particles.

Some example second monomers are of Formula (III).

$$CH_2=CR^1-(CO)-O-Y-R^2 \tag{III}$$

In this formula, group $R^1$ is hydrogen or methyl. In many embodiments, $R^1$ is hydrogen. Group Y is a single bond, alkylene, oxyalkylene, or poly(oxyalkylene). Group $R^2$ is a carbocyclic group or heterocyclic group. These second monomers tend to be miscible with the first monomer of Formula (I) in the second phase but are not miscible with the first phase.

As used herein, the term "alkylene" refers to a divalent group that is a radical of an alkane and includes groups that are linear, branched, cyclic, bicylic, or a combination thereof. As used herein, the term "oxyalkylene" refers to a divalent group that is an oxy group bonded directly to an alkylene group. As used herein, the term "poly(oxyalkylene)" refers to a divalent group having multiple oxyalkylene groups. Suitable Y alkylene and oxyalkylene groups typically have 1 to 20 carbon atoms, 1 to 16 carbon atoms, 1 to 12 carbon atoms, 1 to 10 carbon atoms, 1 to 8 carbon atoms, 1 to 6 carbon atoms, or 1 to 3 carbon atoms. The oxyalkylene is often oxyethylene or oxypropylene. Suitable poly(oxyalkylene) groups typically have 2 to 20 carbon atoms, 2 to 16 carbon atoms, 2 to 12 carbon atoms, 2 to 10 carbon atoms, 2 to 8 carbon atoms, 2 to 6 carbon atoms, or 2 to 4 carbon atoms. The poly(oxyalkylene) is often poly (oxyethylene), which can be referred to as poly(ethylene oxide) or poly(ethylene glycol).

Carbocyclic $R^2$ groups can have a single ring or can have multiple rings such as fused rings or bicylic rings. Each ring can be saturated, partially unsaturated, or unsaturated. Each ring carbon atom can be unsubstituted or substituted with alkyl groups. Carbocyclic groups often have 5 to 12 carbon atoms, 5 to 10 carbon atoms, or 6 to 10 carbon atoms. Examples of carbocyclic groups include, but are not limited to, phenyl, cyclohexyl, cyclopentyl, isobornyl, and the like. Any of these carbocyclic groups can be substituted with an alkyl group having 1 to 20 carbon atoms, 1 to 10 carbon atoms, 1 to 6 carbon atoms, or 1 to 4 carbon atoms.

Heterocyclic $R^2$ groups can have a single ring or multiple rings such as fused rings or bicyclic rings. Each ring can be saturated, partially unsaturated, or unsaturated. The heterocyclic group contains at least one heteroatom selected from oxygen, nitrogen, or sulfur. The heterocyclic group often has 3 to 10 carbon atoms and 1 to 3 heteroatoms, 3 to 6 carbon atoms and 1 to 2 heteroatoms, or 3 to 5 carbon atoms and 1 to 2 heteroatoms. Examples of heterocyclic rings include, but are not limited to, tetrahydrofurfuryl.

Exemplary monomers of Formula (III) for use as the second monomer include, but are not limited to, benzyl (meth)acrylate, 2-phenoxyethyl (meth)acrylate (commercially available from Sartomer under the trade designation SR339 and SR340), isobornyl (meth)acrylate, tetrahydrofurfuryl (meth)acrylate (commercially available from Sartomer under the trade designation SR285 and SR203), 3,3,5-trimethylcyclohexyl (meth)acrylate (commercially available from Sartomer under the trade designation CD421 and CD421A), and ethoxylated nonyl phenol acrylate (commercially available from Sartomer under then trade designation SR504, CD613, and CD612).

Other example second monomers are alkyl (meth)acrylates of Formula (IV).

$$CH_2=CR^1-(CO)-O-R^3 \qquad (IV)$$

In Formula (IV), group $R^1$ is hydrogen or methyl. In many embodiments, $R^1$ is hydrogen. Group $R^3$ is a linear or branched alkyl having 1 to 20 carbon atoms, 1 to 10 carbon atoms, 1 to 6 carbon atoms, or 1 to 4 carbon atoms. These second monomers tend to be miscible with the first monomer of Formula (I) in the second phase but are not miscible with the first phase.

Examples of alkyl (meth)acrylates of Formula (IV) include, but are not limited to, methyl (meth)acrylate, ethyl (meth)acrylate, n-propyl (meth)acrylate, isopropyl (meth) acrylate, n-butyl (meth)acrylate, isobutyl (meth)acrylate, n-pentyl (meth)acrylate, 2-methylbutyl (meth)acrylate, n-hexyl (meth)acrylate, 4-methyl-2-pentyl (meth)acrylate, 2-ethylhexyl (meth)acrylate, 2-methylhexyl (meth)acrylate, n-octyl (meth)acrylate, isooctyl (meth)acrylate, 2-octyl (meth)acrylate, isononyl (meth)acrylate, isoamyl (meth) acrylate, n-decyl (meth)acrylate, isodecyl (meth)acrylate, 2-propylheptyl (meth)acrylate, isotridecyl (meth)acrylate, isostearyl (meth)acrylate, octadecyl (meth)acrylate, 2-octyldecyl (meth)acrylate, dodecyl (meth)acrylate, lauryl (meth) acrylate, and heptadecanyl (meth)acrylate.

In some embodiments, the only monomers in the monomer composition are the first monomer of Formula (II) and the second monomer of Formula (III), Formula (IV), or both. Any suitable amounts of the first monomer and second monomer can be used provided that the monomer composition contains at least 10 weight percent of the first monomer of Formula (II). The addition of a second monomer of Formula (III), Formula (IV), or both tends to increase the hydrophobicity of the porous polymeric particles. The monomer composition often contains 10 to 90 weight percent of the first monomer and 10 to 90 weight percent of the second monomer based on a total weight of monomers in the monomer composition. For example, the second phase can contain 20 to 80 weight percent of the first monomer and 20 to 80 weight percent of the second monomer, 25 to 75 weight percent of the first monomer and 25 to 75 weight percent of the second monomer, 30 to 70 weight percent of the first monomer and 30 to 70 weight percent of the second monomer, or 40 to 60 weight percent of the first monomer and 40 to 60 weight percent of the second monomer based on a total weight of monomers in the monomer composition.

Depending on the final use of the polymeric particles prepared, it can be desirable to include at least one hydrophilic second monomer in the monomer composition. The addition of a hydrophilic second monomer tends to make the polymeric particles more suitable for applications where the particles will be exposed to aqueous-based materials such as aqueous-based samples. Additionally, the use of a hydrophilic second monomer allows the porous polymeric particles to be dispersed in water more easily during the preparation of the porous article using, for example, a wetlaid process. Hydrophilic second monomers are selected so that they are not miscible with the first phase. These monomers may or may not be miscible with the first monomer of Formula (II).

Some example hydrophilic second monomers are hydroxyl-containing monomers of Formula (V).

$$CH_2=CR^1-(CO)-O-R^4 \qquad (V)$$

In Formula (V), group $R^1$ is hydrogen or methyl. In many embodiments, $R^1$ is hydrogen. Group $R^4$ is an alkyl substituted with one or more hydroxyl groups or a group of formula $(CH_2CH_2O)_qCH_2CH_2OH$ where q is an integer equal to at least 1. The alkyl group typically has 1 to 10 carbon atoms, 1 to 6 carbon atoms, 1 to 4 carbon atoms, or 1 to 3 carbon atoms. The number of hydroxyl groups is often in a range of 1 to 3. The variable q is often in a range of 1 to 20, in a range of 1 to 15, in a range of 1 to 10, or in a range of 1 to 5. In many embodiments, the second monomer of Formula (IV) has a single hydroxyl group.

Example monomers of Formula (V) include, but are not limited to, 2-hydroxyethyl (meth)acrylate, 2-hydroxypropyl (meth)acrylate, 3-hydroxypropyl (meth)acrylate, and 4-hydroxybutyl (meth)acrylate), 2-hydroxylbutyl (meth)acrylate, polyethylene glycol mono(meth)acrylate (for example, monomers commercially available from Sartomer (Exton, Pa., USA) under the trade designation CD570, CD571, and CD572), and glycol mono(meth)acrylate.

Other example hydrophilic second monomers are hydroxyl-containing monomers of Formula (VI).

$$CH_2=CR^1-(CO)-O-R^5-O-Ar \qquad (VI)$$

In Formula (VI), group $R^1$ is hydrogen or methyl. In many embodiments, $R^1$ is hydrogen. Groups $R^5$ is an alkylene substituted with at least one hydroxyl group. Suitable alkylene groups often have 1 to 10 carbon atoms, 1 to 6 carbon atoms or 1 to 4 carbon atoms. The alkylene group $R^5$ can be substituted with 1 to 3 hydroxyl groups but is often substituted with a single hydroxyl group. The group Ar is an aryl group having 6 to 10 carbon atoms. In many embodiments, the Ar group is phenyl. One example monomer of Formula (VI) is 2-hydroxy-2-phenoxypropyl (meth)acrylate.

If the second monomer is of Formula (V) or (VI), which are hydroxyl-containing monomers, the amount of this monomer that can be combined with the first monomer of Formula (I) is often no greater than 2 weight percent based on a total weight of monomers in the monomer composition. If greater than about 2 weight percent of the second monomer of Formula (V) or (VI) is used, the resulting polymeric particles tend to have diminished porosity.

Other hydrophilic monomers can be used as the second monomers in larger quantities than the second monomers of Formula (V) or (VI) without diminishing the porosity of the resulting polymeric particles. For example, sulfonic acid-containing monomers of Formula (VII) can be included in the monomer composition along with the first monomer of Formula (II) or a salt thereof.

$$CH_2=CR^1-(CO)-O-R^6-SO_3H \qquad (VII)$$

In Formula (VII), group $R^1$ is hydrogen or methyl. In many embodiments, $R^1$ is hydrogen. Group $R^6$ is an alkylene having 1 to 10 carbon atoms, 1 to 6 carbon atoms, or 1 to 4 carbon atoms. Examples of sulfonic acid-containing monomers of Formula (VII) include, but are not limited to, sulfoethyl (meth)acrylate and sulfopropyl (meth)acrylate. Depending on the pH conditions, these second monomers can impart an ionic (for example, anionic) character to the porous polymeric particles. The counter ion is often a cation of such as an alkali metal ion, an alkaline earth metal ion, an ammonium ion, or an alkyl substituted ammonium ions such as tetraalkyl ammonium ion.

If the second monomer is a sulfonic acid-containing monomer of Formula (VII), the monomer composition can contain up to 20 weight percent of this monomer based on a total weight of monomers in the monomer composition. In some embodiments, the only monomers in the monomer composition are the first monomer of Formula (II) and the second monomer of Formula (VII). The monomer composition often contains 80 to 99 weight percent of the first monomer of Formula (II) and 1 to 20 weight percent of the second monomer of Formula (VII) based on a total weight of monomers in the monomer composition. For example, the monomer composition can contain 85 to 99 weight percent of the first monomer and 1 to 15 weight percent of the second monomer, 90 to 99 weight percent of the first monomer and 1 to 10 weight percent of the second monomer, and 95 to 99 weight percent of the first monomer and 1 to 5 weight percent of the second monomer based on a total weight of monomers in the monomer composition.

In other embodiments, the monomer composition includes a first monomer of Formula (II) and two second monomers. The two second monomers are a sulfonic acid-containing monomer, such as those of Formula (VII), and a hydroxyl-containing monomer, such as those of Formula (V) or (VI). When the hydroxyl-containing monomer is combined with a sulfonic acid-containing monomer, higher amounts of the hydroxyl-containing monomer can be added to the monomer composition without substantially decreasing the porosity of the resulting polymeric particles. That is, the amount of the hydroxyl-containing monomer can be greater than 2 weight percent based on the weight of the monomers in the monomer composition. The monomer composition often contains 80 to 99 weight percent of the first monomer of Formula (II) and 1 to 20 weight percent of the second monomer, wherein the second monomer is a mixture of the sulfonic acid-containing monomer and the hydroxyl-containing monomer. Up to 50 weight percent, up to 40 weight percent, up to 20 weight percent, or up to 10 weight percent of the second monomer can be the hydroxyl-containing monomer.

Other second monomers that can impart an ionic (for example, anionic) character to the porous polymeric particles have a carboxylic acid group (—COOH). Examples of such monomers include, but are not limited to, (meth)acrylic acid, maleic acid, and ß-carboxyethyl acrylate. If a monomer having a carboxylic acid group is added, this monomer typically is present in an amount no greater than 20 weight percent, no greater than 15 weight percent, no greater than 10 weight percent, or no greater than 5 weight percent based on the total weight of monomers in the monomer composition. For example, the monomer composition often contains 80 to 99 weight percent of the first monomer of Formula (II) and 1 to 20 weight percent of the second monomer having a carboxylic acid group. For example, the monomer composition can contain 85 to 99 weight percent of the first monomer and 1 to 15 weight percent of the second monomer, 90 to 99 weight percent of the first monomer and 1 to 10 weight percent of the second monomer, and 95 to 99 weight percent of the first monomer and 1 to 5 weight percent of the second monomer based on a total weight of monomers in the monomer composition.

Still other hydrophilic monomers are those of Formula (VIII)

$$CH_2=CR^1-(CO)-O-R^7-N(R^8)_3^+X^- \qquad (VIII)$$

having a quaternary ammonium group. The group $R^7$ is an alkylene having 1 to 10 carbon atoms, 1 to 6 carbon atoms, or 1 to 4 carbon atoms. The group $R^8$ is an alkyl having 1 to 4 carbon atoms or 1 to 3 carbon atoms. The anion $X^-$ can be any anion but is often a halide such as chloride. Alternatively the anion can be a sulfate and be associated with two ammonium-containing cationic monomers.

Examples include, but are not limited to, (meth)acrylamidoalkyltrimethylammonium salts (for example, 3-methacrylamidopropyltrimethylammonium chloride and 3-acrylamidopropyltrimethylammonium chloride) and (meth) acryloxyalkyltrimethylammonium salts (for example, 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate). Depending on the pH conditions, these third monomers can impart an ionic (for example, cationic) character to the porous polymeric particles.

If a second monomer of Formula (VIII) is added, this monomer typically is present in an amount no greater than 20 weight percent, no greater than 15 weight percent, no greater than 10 weight percent, or no greater than 5 weight percent based on the total weight of monomers in the monomer composition. For example, the monomer composition often contains 80 to 99 weight percent of the first monomer of Formula (II) and 1 to 20 weight percent of the second monomer of Formula (VIII). For example, the monomer composition can contain 85 to 99 weight percent of the first monomer and 1 to 15 weight percent of the second monomer, 90 to 99 weight percent of the first monomer and 1 to 10 weight percent of the second monomer, and 95 to 99 weight percent of the first monomer and 1 to 5 weight percent of the second monomer based on a total weight of monomers in the monomer composition.

Often if an ionic monomer is added such as one having a carboxylic acid group or a salt thereof, a sulfonic acid group or a salt thereof (such as of Formula (VII)), or an ammonia group (such as of Formula (VIII)), the ionic monomer is often present in low amounts such as in a range of 1 to 10 weight percent, in a range of 1 to 5 weight percent, or in a range of 1 to 3 percent based on the total weight of monomers in the monomer composition. Particularly when the preparation of porous polymeric particles having an average diameter less than about 10 micrometers, less than about 5 micrometers, less than about 4 micrometers, or less than about 3 micrometers are desired, lower concentrations of the ionic monomers in the monomer composition may be preferred. For use with hydrophobic materials or nonionic materials, it may be preferable to have monomer compositions that are free or substantially free of ionic monomers. As used herein in reference to the amount of ionic monomers, "substantially free" means that no such monomer is intentionally added or is added at an amount no greater than 1 weight percent, no greater than 0.5 weight percent, no greater than 0.2 weight percent, or no greater than 0.1 weight percent based on the total weight of monomers in the monomer composition.

In some embodiments, it is preferable that the monomer composition contains only a monomer of Formula (II) or a mixture of a first monomer of Formula (II) and a second monomer of Formula (III) added to increase the hydrophobicity of the porous polymeric particles. For example, some monomer compositions often contains 10 to 90 weight percent of the first monomer and 10 to 90 weight percent of the second monomer based on a total weight of monomers in the monomer composition. For example, the monomer composition can contain 20 to 80 weight percent of the first monomer and 20 to 80 weight percent of the second monomer, 25 to 75 weight percent of the first monomer and 25 to 75 weight percent of the second monomer, 30 to 70 weight percent of the first monomer and 30 to 70 weight percent of the second monomer, or 40 to 60 weight percent of the first monomer and 40 to 60 weight percent of the second monomer.

The monomer composition can optionally contain a third monomer with at least two polymerizable groups. The polymerizable groups are typically (meth)acryloyl groups. In many embodiments, the third monomer has two or three (meth)acryloyl groups. The third monomer typically is not miscible with the first phase and may or may not be miscible with the first monomer of Formula (II).

Some third monomers have a hydroxyl group. Such monomers can function as crosslinkers like the first monomer of Formula (II) but can provide polymeric particles with increased hydrophilic character. An example hydroxyl-containing third monomer is glycerol di(meth)acrylate.

Some third monomers are selected to have at least three polymerizable groups. Such third monomers can be added to provide more rigidity to the resulting polymeric particles. The addition of these third monomers tends to minimize swelling of the polymeric particles when exposed to water. Suitable third monomers include, but are not limited to, ethoxylated trimethylolpropane tri(meth)acrylates such as ethoxylated (15) trimethylolpropane triacrylate (commercially available under the trade designation SR9035 from Sartomer) and ethoxylated (20) trimethylolpropane triacrylate (commercially available under the trade designation SR415 from Sartomer); propoxylated trimethylolpropane tri(meth)acrylates such as propoxylated (3) trimethylolpropane triacrylate (commercially available under the trade designation SR492 from Sartomer) and propoxylated (6) trimethylolpropane triacrylate (commercially available under the trade designation CD501 from Sartomer); tris(2-hydroxyethyl) isocyanurate tri(meth)acrylates such as tris (2-hydroxyethyl) isocyanurate triacrylate (commercially available under the trade designations SR368 and SR368D from Sartomer); and propoxylated glyceryl tri(meth)acrylates such as propoxylated (3) glycerol triacrylate (commercially available under the trade designation SR9020 and SR9020HP from Sartomer).

When a third monomer is present in the monomer composition, any suitable amount can be used. The third monomer is often used in an amount up to 20 weight percent based on the total weight of monomers in the monomer composition. In some embodiments, the amount of the third monomer is up to 15 weight percent, up to 10 weight percent, or up to 5 weight percent.

In some embodiments, the monomer composition contains at least 10 weight percent, at least 20 weight percent, at least 30 weight percent, at least 35 weight percent, at least 40 weight percent, at last 45 weight percent, at least 50 weight percent, at least 55 weight percent, at least 60 weight percent, at least 65 weight percent, at least 70 weight percent, at least 75 weight percent at least 80 weight percent, at least 90 weight percent, or at least 95 weight percent of the first monomer of Formula (II). The remaining amount of the monomer composition can include any combination of the second and third monomers described above. In some embodiments, any remaining amount is a monomer of Formula (III).

The monomer composition often contains 10 to 100 weight percent of the first monomer, 0 to 90 weight percent of the second monomer, and 0 to 20 weight percent of the third monomer based on a total weight of monomers in the monomer composition. For example, the monomer composition can contain 10 to 90 weight percent of the first monomer, 10 to 90 weight percent of the second monomer, and 0 to 20 weight percent of the third monomer. The monomer composition can contain 10 to 89 weight percent of the first monomer, 10 to 89 weight percent of the second monomer, and 1 to 20 weight percent of the third monomer based on a total weight of the monomer composition.

In most embodiments, the porous polymeric particles that are prepared using a second monomer or third monomer that is hydrophilic are particularly suitable to absorb/adsorb moisture.

In addition to the monomer composition, the second phase contains poly(propylene glycol), which functions as a porogen. The poly(propylene glycol) is soluble in the monomer composition within the second phase but is dispersible within the first phase. Stated differently, the poly(propylene glycol) is completely miscible with the second phase and partially miscible with the first phase. The poly(propylene glycol) is removed after polymerization of the monomer composition to provide pores (for example, void volumes or free volumes) in the polymeric particle. The poly(propylene glycol) does not have any polymerizable groups (i.e., it is not a monomer) and, in general, is not covalently attached to the polymeric particles that forms within the second phase. It is believed that some of the poly(propylene glycol) become entrained within the polymerized product. It is further believed that some of the poly(propylene glycol) is positioned on the interface between the first phase and the second phase as the polymerized product is formed in the second phase. The presence of the poly(propylene glycol) at the surface of the forming polymerized product results in the formation of a polymeric particle having surface porosity. The surface porosity can be seen from electron micrographs of polymeric particles made according to the disclosure, in FIG. 8A. A higher magnification of the polymeric particles of FIG. 8A can be seen in FIG. 8B.

The second phase can contain up to 50 weight percent poly(propylene glycol). If higher amounts of the poly(propylene glycol) are used, there may be an insufficient amount of the monomer composition included in the second phase to form polymeric particles that are uniformly shaped. In many embodiments, the second phase can contain up to 45 weight percent, up to 40 weight percent, up to 35 weight percent, up to 30 weight percent, or up to 25 weight percent poly (propylene glycol) based on a total weight of the second phase. The second phase typically contains at least 5 weight percent poly(propylene glycol). If lower amounts of the poly(propylene glycol) are used, the porosity of the resulting polymeric particles may be insufficient. The second phase typically can contain at least 10 weight percent, at least 15 weight percent, or at least 20 weight percent poly(propylene glycol). In some embodiments, the second phase contains 5 to 50 weight percent, 10 to 50 weight percent, 10 to 40 weight percent, 10 to 30 weight percent, 20 to 50 weight percent, 20 to 40 weight percent, or 25 to 35 weight percent poly(propylene glycol) based on the total weight of the second phase.

In some embodiments, the second phase contains 50 to 90 weight percent monomer composition and 10 to 50 weight percent poly(propylene glycol), 60 to 90 weight percent monomer composition and 10 to 40 weight percent poly(propylene glycol), 50 to 80 weight percent monomer composition and 20 to 50 weight percent poly(propylene glycol), or 60 to 80 weight percent monomer composition and 20 to 40 weight percent poly(propylene glycol) based on a total weight of the second phase.

In addition to the monomer composition and poly(propylene glycol), the second phase often contains an initiator for free radical polymerization of the monomer composition. Any suitable initiator known in the art can be used. The initiator can be a thermal initiator, a photoinitiator, or both. The specific initiator used is often selected based on its solubility in the second phase. The initiator is often used at a concentration of 0.1 to 5 weight percent, 0.1 to 3 weight percent, 0.1 to 2 weight percent, or 0.1 to 1 weight percent based on the weight of monomers in the monomer composition.

When a thermal initiator is added to the reaction mixture, polymeric particles can be formed at room temperature (i.e., 20 to 25 degrees Celsius) or at an elevated temperature. The temperature needed for polymerization often depends on the particular thermal initiator used. Examples of thermal initiators include organic peroxides and azo compounds.

When a photoinitiator is added to the reaction mixture, polymeric particles can be formed by the application of actinic radiation. Suitable actinic radiation includes electromagnetic radiation in the infrared region, visible region, ultraviolet region, or a combination thereof.

Examples of photoinitiators suitable in the ultraviolet region include, but are not limited to, benzoin, benzoin alkyl ethers (for example, benzoin methyl ether and substituted benzoin alkyl ethers such anisoin methyl ether), phenones (for example, substituted acetophenones such as 2,2-dimethoxy-2-phenylacetophenone and substituted alpha-ketols such as 2-methyl-2-hydroxypropiophenone), phosphine oxides, polymeric photoinitiators, and the like.

Commercially available photoinitiators include, but are not limited to, 2-hydroxy-2-methyl-1-phenyl-propane-1-one (for example, commercially available under the trade designation DAROCUR 1173 from Ciba Specialty Chemicals), a mixture of 2,4,6-trimethylbenzoyl-diphenyl-phosphine oxide and 2-hydroxy-2-methyl-1-phenyl-propan-1-one (for example, commercially available under the trade designation DAROCUR 4265 from Ciba Specialty Chemicals), 2,2-dimethoxy-1,2-diphenylethan-1-one (for example, commercially available under the trade designation IRGACURE 651 from Ciba Specialty Chemicals), a mixture of bis(2,6-dimethoxybenzoyl)-2,4,4-trimethyl-pentylphosphine oxide and 1-hydroxy-cyclohexyl-phenyl-ketone (for example, commercially available under the trade designation IRGACURE 1800 from Ciba Specialty Chemicals), a mixture of bis(2,6-dimethoxybenzoyl)-2,4,4-trimethyl-pentylphosphine oxide (for example, commercially available under the trade designation IRGACURE 1700 from Ciba Specialty Chemicals), 2-methyl-1[4-(methylthio)phenyl]-2-morpholinopropan-1-one (for example, commercially available under the trade designation IRGACURE 907 from Ciba Specialty Chemicals), 1-hydroxy-cyclohexyl-phenyl-ketone (for example, commercially available under the trade designation IRGACURE 184 from Ciba Specialty Chemicals), 2-benzyl-2-(dimethylamino)-1-[4-(4-morpholinyl)phenyl]-1-butanone (for example, commercially available under the trade designation IRGACURE 369 from Ciba Specialty Chemicals), bis(2,4,6-trimethylbenzoyl)-phenylphosphine oxide (for example, commercially available under the trade designation IRGACURE 819 from Ciba Specialty Chemicals), ethyl 2,4,6-trimethylbenzoyldiphenyl phosphinate (for example, commercially available from BASF, Charlotte, N.C. under the trade designation LUCIRIN TPO-L), and 2,4,6-trimethylbenzoyldiphenylphosphine oxide (for example, commercially available from BASF, Charlotte, N.C. under the trade designation LUCIRIN TPO).

The reaction mixture often includes at least 5 weight percent of the second phase (dispersed phase) and up to 95 weight percent of the first phase (continuous phase). In some embodiments, the reaction mixture contains 5 to 40 weight percent second phase and 60 to 95 weight percent first phase, 5 to 30 weight percent second phase and 70 to 95 weight percent first phase, 10 to 30 weight percent second phase and 70 to 90 weight percent first phase, or 5 to 20 weight percent second phase and 80 to 95 weight percent first phase. The weight percents are based on a total weight of the reaction mixture.

To prepare the polymeric particles or beads, droplets of the second phase are formed in the first phase. The components of the second phase are often mixed together prior to addition to the first phase. For example, the monomer composition, initiator, and the poly(propylene glycol) can be blended together and then this blended composition, which is the second phase, can be added to the first phase. The resulting reaction mixture is often mixed under high shear to form a micro-emulsion. The size of the dispersed second phase droplets can be controlled by the amount of shear or the mixing rate. The size of the droplets can be determined by placing a sample of the mixture under an optical microscope prior to polymerization. Although any desired droplet size can be used, the average droplet diameter is often less than 500 micrometers, less than 200 micrometers, less than 100 micrometers, less than 50 micrometers, less than 25 micrometers, less than 10 micrometers, or less than 5 micrometers. For example, the average droplet diameter can be in the range of 1 to 500 micrometers, 1 to 200 micrometers, 1 to 100 micrometers, 5 to 100 micrometers, 5 to 50 micrometers, 5 to 25 micrometers, or 5 to 10 micrometers.

If a photoinitiator is used, the reaction mixture is often spread on a non-reactive surface at a thickness that can be penetrated by the desired actinic radiation. The reaction mixture is spread using methods that do not cause the droplets to coalesce. For example, the reaction mixture can be formed using an extrusion method. Often, the actinic radiation is in the ultraviolet region of the electromagnetic spectrum. If the ultraviolet radiation is applied from only the top surface of the reaction mixture layer, the thickness of the layer can be up to about 10 millimeters. If the reaction mixture layer is exposed to ultraviolet radiation from both the top and bottom surfaces, the thickness can be greater such as up to about 20 millimeters. The reaction mixture is subjected to the actinic radiation for a time sufficient to react the monomer composition and form polymeric particles. The reaction mixture layer is often polymerized within 5 minutes, within 10 minutes, within 20 minutes, within 30 minutes, within 45 minutes, or within 1 hour depending on the intensity of the actinic radiation source and the thickness of the reaction mixture layer.

If a thermal initiator is used, the droplets can be polymerized while continuing to mix the reaction mixture. Alternatively, the reaction mixture can be spread on a non-reactive surface to any desired thickness. The reaction mixture layer can be heated from the top surface, from the bottom surface, or both to form the polymeric particles. The thickness is often selected to be comparable to that use with the use of actinic radiation such as ultraviolet radiation.

In many embodiments, a photoinitiator is preferred over a thermal initiator because lower temperatures can be used for polymerization. That is, the use of actinic radiation such as ultraviolet radiation can be used to minimize degradation of various components of the reaction mixture that might be sensitive to temperatures needed for use with thermal initiators. Further, the temperatures typically associated with the use of thermal initiators may undesirably alter the solubility of the various components of the reaction mixture between the first phase and the dispersed second phase.

During the polymerization reaction, the monomer composition reacts within the second phase droplets suspended in the first phase. As polymerization progresses, the poly(propylene glycol) included in the second phase gets partially entrained within the polymerized product. Although it is possible that some portion of the poly(propylene glycol) can be covalently attached to the polymeric product through a chain transfer reaction, preferably the poly(propylene glycol) is not bonded to the polymeric product. The polymerized product is in the form of particles. In some embodiments, the particles are polymeric beads having a relatively uniform size and shape.

After formation of the polymerized product (i.e., polymeric particles containing entrained poly(propylene glycol)), the polymerized product can be separated from the first phase. Any suitable separation method can be used. For example, water is often added to lower the viscosity of the first phase. Particles of the polymerized product can be separated from the other components by decantation, filtration, or centrifugation. The particles of the polymerized product can be further washed by suspending them in water and collecting them a second time by decantation, filtration, or centrifugation.

The particles of the polymerized product can then be subjected to one or more washing steps to remove the poly(propylene glycol) porogen. Suitable solvents for removing the poly(propylene glycol) include, for example, acetone, methyl ethyl ketone, toluene, and alcohols such as ethanol, n-propanol, or iso-propanol. Stated differently, the entrained poly(propylene glycol) is removed from the polymerized product using solvent extraction methods. Pores are created where the poly(propylene glycol) previously resided.

In many embodiments, the resulting porous polymeric particles (the polymerized product after removal of the poly(propylene glycol) porogen) have an average diameter that is less than 500 micrometers, less than 200 micrometers, less than 100 micrometers, less than 50 micrometers, less than 25 micrometers, less than 10 micrometers, or less than 5 micrometers. For example, the porous polymeric particles can have an average diameter in the range of 1 to 500 micrometers, 1 to 200 micrometers, 1 to 100 micrometers, 1 to 50 micrometers, 1 to 25 micrometers, 1 to 10 micrometers, or 1 to 5 micrometers. The particles are often in the form of beads.

The polymeric particles usually have multiple pores distributed over the surface of the particles. In some embodiments, the polymeric particles are hollow in addition to having multiple pores distributed over the surface of the particles. After removal of the poly(propylene glycol) porogen, the resulting polymeric particles tend to be more porous than polymeric particles prepared using a first phase that is predominately water. The polymeric core typically has pores having an average size in a range of 1 to 200 nanometers.

Figure 9A:
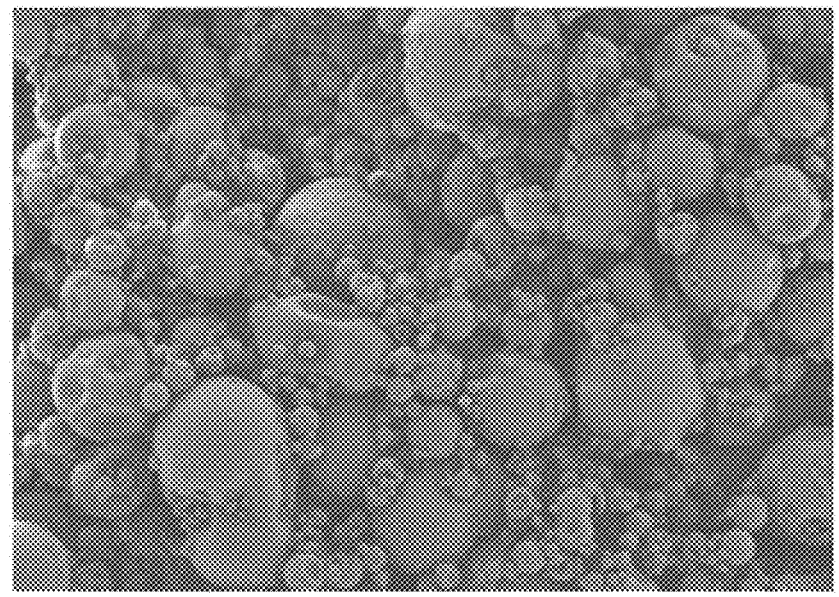
FIG. 9A is the scanning electron micrograph (SEM) of polymeric composite particles prepared as described in Preparatory Example 2.

Referring to FIG. 9A, an electron micrograph is provided of the polymeric composite particles having a coating layer. A higher magnification of the polymeric particles of FIG. 9A can be seen in FIG. 9B.

As discussed above, the porous polymeric particles can be made to have hydrophilic character, hydrophobic character, or both. Accordingly, in any embodiment, the porous polymeric composite particles in a matrix comprise hydrophilic particles, hydrophobic particles, or a combination of hydrophilic particles and hydrophobic particles. In certain embodiments, the porous polymeric composite particles comprise a unimodal particle size distribution, while in other embodiments the porous polymeric composite particles comprise a multimodal particle size distribution, such as a bimodal particle size distribution.

In a third aspect, a method of determining a minimum temperature of a composition is provided. The method includes a) providing a composition comprising a plurality of polymeric composite particles disposed in a matrix, wherein the polymeric composite particles include a porous polymeric core and a fragrance positioned within the porous polymeric core. The method further includes b) heating the composition; c) releasing at least a portion of the fragrance as a vapor from the porous polymeric core of the polymeric composite particles at or above the minimum temperature; and d) detecting at least a portion of the fragrance vapor in a location outside of the matrix.

Figure 10:
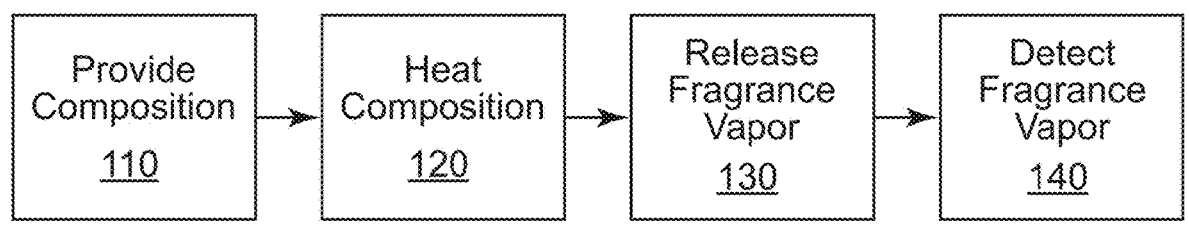
FIG. 10 is a flow chart of an exemplary method of detecting a minimum temperature according to the disclosure.

Referring to FIG. 10, a flow chart of an exemplary method of detecting a minimum temperature according to the disclosure is provided. In particular, the method includes 110 providing a composition comprising a plurality of polymeric composite particles disposed in a matrix, wherein the polymeric composite particles include a porous polymeric core and a fragrance positioned within the porous polymeric core. The method further includes 120 heating the composition; 130 releasing at least a portion of the fragrance as a vapor from the porous polymeric core of the polymeric composite particles at or above the minimum temperature; and 140 detecting at least a portion of the fragrance vapor in a location outside of the matrix.

Fragrances are often noticed by living beings, such as human beings or other mammals, due to their odors being detectable using the sense of smell. In many embodiments, the fragrance vapor is detected by a living being, such as at a concentration of at least 0.5 parts per billion (ppb). Different fragrances are generally detectable by living beings at various minimum amounts depending on the functional groups of the fragrance, thus the fragrance vapor is optionally detected by a living being at a concentration of at least 1 ppb, or at least 5 ppb, or at least 10 ppb, or at least 50 ppb, or at least 500 ppb, or at least 1 part per million (ppm), or at least 500 ppm, depending on the average threshold odor provided by the particular fragrance. In certain embodiments, the fragrance vapor is detected by a gas sensor, at a concentration of at least 1 part per million. A fragrance vapor detected by a gas sensor is limited only by the chemical compound detection limit of the gas sensor, not an extent of odor provided by the particular fragrance. The fragrance vapor is thus optionally detected by a gas sensor at a concentration of at least 1 ppm, or at least 2 ppm, or at least 5 ppm, or at least 10 ppm, or at least 50 ppm, or at least 100 ppm, or at least 500 ppm.

Advantageously, the release of fragrance vapor from polymeric composite particles can be tuned according to a desired application. For instance, different materials are considered to overheat at various temperatures, thus a coating layer on the polymeric composite particles may be selected to soften and release fragrance vapor from the polymeric composite particles at or below a temperature that qualifies as overheating of the material of interest. In certain embodiments, it is not an issue of overheating but rather determining that a desired elevated temperature has been reached (e.g., indicating the extent of reaction in an exothermic chemical reaction). In certain embodiments, the matrix comprises a heat-debondable adhesive. When the adhesive matrix is not visible from an exterior of the composition, release of fragrance from the polymeric composite particles provides an indicator that a debonding temperature has been achieved and the adhesive can be separated from one or more materials to which it had been adhered.

The coating layer material is optionally selected to release fragrance vapor from the polymeric core of the polymeric composite particles at a minimum temperature of at least 30 degrees Celsius, or at least 45 degrees Celsius, or at least 50 degrees Celsius, or at least 60 degrees Celsius, or at least 70 degrees Celsius, or at least 80 degrees Celsius, or at least 90 degrees Celsius, or at least 100 degrees Celsius, or at least 110 degrees Celsius, or at least 120 degrees Celsius, or at least 130 degrees Celsius. Stated another way, the minimum temperature at which fragrance is released as a vapor from the porous polymeric core of the polymeric composite particles is optionally between 30 degrees Celsius and 150 degrees Celsius, or between 30 degrees Celsius and 100 degrees Celsius, or between 30 degrees Celsius and 50 degrees Celsius, or between 45 degrees Celsius and 130 degrees Celsius, or between 45 degrees Celsius and 80 degrees Celsius, or between 60 degrees Celsius and 150 degrees Celsius, or between 60 degrees Celsius and 120 degrees Celsius, or between 100 degrees Celsius and 150 degrees Celsius, or between 100 degrees Celsius and 130 degrees Celsius, or about 120 degrees Celsius. In certain embodiments, to trigger the release of fragrance vapor via elevated temperature, the composition is heated by electrical resistance, conductive heat, radiative heat, convective heat, or a combination thereof. For example and without limitation, in some embodiments the composition is heated by a heat gun, a lamp, a torch, a heated liquid, an exothermic chemical reaction, solar heat, body heat, or a combination thereof.

Figure 11:
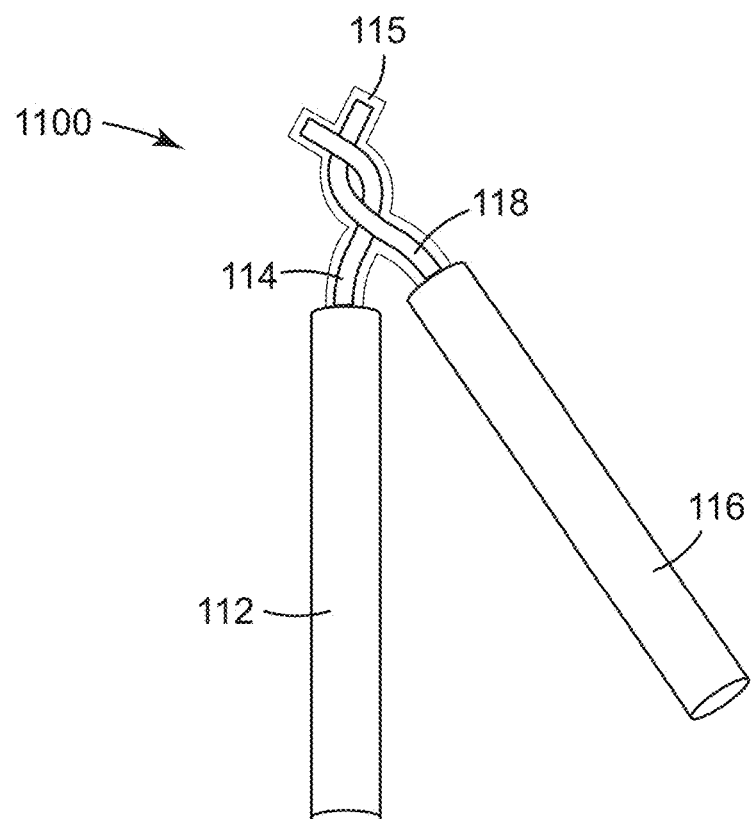
FIG. 11 is a schematic of an electrical wire connection coated with an exemplary composition according to the disclosure.

One example includes electrical components, which can overheat if excessive resistance is generated. Referring to FIG. 11, a schematic of an electrical wire connection coated with an exemplary composition according to the disclosure is provided. The electrical wire connection 1100 comprises a first wire 114 extending from a first wire coating 112, and a second wire 118 extending from a second wire coating 116. The first wire 114 and the second wire 118 are twisted together to form a wire connection. The first wire 114 and the second wire 118 are coated with a composition 115 according to the first aspect of the present disclosure. In particular, the composition 115 comprises a matrix and a plurality of polymeric composite particles disposed in the matrix (not shown). Accordingly, if sufficient resistance is generated in the electrical wire connection 1100, the composition 115 will heat up and fragrance vapor will be released from the polymeric composite particles into the ambient air, to provide a detectable indication of the temperature of the composition without requiring a line of sight to the composition.

In some embodiments, the composition according to aspects of the disclosure is disposed in a blind location. Typical blind locations include for example and without limitation, within a housing, behind a wall, behind a ceiling, behind a floor, or a combination thereof, or behind an opaque material. Opaque materials include for example and without limitation, a film, a sheet, a foam, a nonwoven material, a woven material, concrete, metal, ceramic, drywall, wood, plastic, cloth, or combinations thereof.

As noted above, in certain embodiments, the polymeric composite particles are configured to release fragrance vapor from the polymeric core of the polymeric composite particles upon contact with a solvent, such as water or acetone. The solvent selection will depend on the shell composition. The solvent can swell the shell, dissolve the shell, or combinations thereof.

Various embodiments are provided that include a composition, a polymeric composite particle, and a method of determining a minimum temperature of a composition.

Embodiment 1 is a composition including a matrix and a plurality of polymeric composite particles disposed in the matrix. The polymeric composite particles include a porous polymeric core and a fragrance positioned within the porous polymeric core.

Embodiment 2 is the composition of embodiment 1, wherein the matrix includes a polymeric material.

Embodiment 3 is the composition of embodiment 1 or embodiment 2, wherein the matrix includes a film, a nonwoven matrix, a woven matrix, a foam, a multilayer construction, a suspension, a gel, or a combination thereof.

Embodiment 4 is the composition of any of embodiments 1 to 3, wherein the matrix includes an adhesive.

Embodiment 5 is the composition of any of embodiments 1 to 4, wherein the matrix includes a heat-debondable adhesive.

Embodiment 6 is the composition of any of embodiments 1 to 5, wherein the polymeric composite particles are not visible from an exterior of the composition.

Embodiment 7 is the composition of any of embodiments 1 to 6, wherein the fragrance includes a water soluble fragrance.

Embodiment 8 is the composition of any of embodiments 1 to 6, wherein the fragrance includes a water insoluble fragrance.

Embodiment 9 is the composition of any of embodiments 1 to 8, wherein the fragrance has a vapor pressure at 25 degrees Celsius of at least 0.05 mmHg.

Embodiment 10 is the composition of any of embodiments 1 to 9, wherein the polymeric composite particles further include a coating layer around the porous polymer core. The coating layer includes a thermoplastic polymer, a wax, or a mixture thereof.

Embodiment 11 is the composition of embodiment 10, wherein the coating layer includes a silicone-based thermoplastic polymer, a (meth)acrylate-based thermoplastic polymer, an olefin-based thermoplastic polymer, a styrene-based thermoplastic polymer, a phenoxy-based resin, polyvinyl pyrrolidone, animal wax, vegetable wax, petroleum wax, hydrogenated vegetable oil, or a combination thereof.

Embodiment 12 is the composition of embodiment 10 or embodiment 11, wherein the coating layer includes a linear thermoplastic polymer.

Embodiment 13 is the composition of any of embodiments 10 to 12, wherein the coating layer includes high density polyethylene.

Embodiment 14 is the composition of any of embodiments 10 to 13, wherein the coating layer has a thickness in a range of 0.1 micrometers to 5 micrometers.

Embodiment 15 is the composition of any of embodiments 10 to 14, wherein the polymeric composite particle has a core-shell configuration with the core being the porous polymeric core particle and the shell being the coating layer.

Embodiment 16 is the composition of any of embodiments 1 to 15, wherein the polymeric composite particles are present in the matrix in an amount of at least 0.05% by weight of the total composition.

Embodiment 17 is the composition of any of embodiments 1 to 16, wherein the polymeric composite particles are present in the matrix in an amount of between 0.05% and 5% by weight of the total composition.

Embodiment 18 is the composition of any of embodiments 1 to 17, wherein the polymeric composite particles are present in the matrix in an amount of between 0.1% and 3% by weight of the total composition.

Embodiment 19 is the composition of any of embodiments 1 to 18, wherein the polymeric core has an average diameter in a range of 1 to 200 micrometers.

Embodiment 20 is the composition of any of embodiments 1 to 19, wherein polymeric core has pores having an average size in a range of 1 to 200 nanometers.

Embodiment 21 is the composition of any of embodiments 1 to 20, wherein the porous polymeric core comprises a polymerized product of a reaction mixture including a) a first phase and b) a second phase dispersed in the first phase. The first phase includes 1) water and a polysaccharide dissolved in the water and/or 2) a surfactant and a compound of Formula (I).

$$HO-(-CH_2-CH(OH)-CH_2-O)_n-H \quad (I)$$

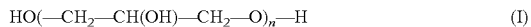

In Formula (I), n is an integer equal to at least 1. A volume of the first phase is greater than a volume of the second phase. The second phase includes 1) a monomer composition comprising a monomer of Formula (II) and 2) a poly(propylene glycol) having a weight average molecular weight of at least 500 grams/mole. The poly(propylene glycol) is removed from the polymerized product to provide the porous polymeric core.

$$CH_2=C(R^1)-(CO)-O[-CH_2-CH_2-O]_p-(CO)-C(R^1)=CH_2 \quad (II)$$

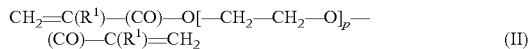

In Formula (II), p is an integer equal to at least 1 and $R^1$ is a hydrogen or alkyl.

Embodiment 22 is the composition of any of embodiments 1 to 21, wherein the matrix is disposed on one or more electrical wires.

Embodiment 23 is a method of determining a minimum temperature of a composition including a) providing a composition comprising a plurality of polymeric composite particles disposed in a matrix, wherein the polymeric composite particles include a porous polymeric core and a fragrance positioned within the porous polymeric core. The method further includes b) heating the composition; c) releasing at least a portion of the fragrance as a vapor from the porous polymeric core of the polymeric composite particles at or above the minimum temperature; and d) detecting at least a portion of the fragrance vapor in a location outside of the matrix.

Embodiment 24 is the method of embodiment 23, wherein the fragrance vapor is detected at a concentration of at least 0.5 parts per billion.

Embodiment 25 is the method of embodiment 23 or embodiment 24, wherein the fragrance vapor is detected at a concentration of at least 1 part per million.

Embodiment 26 is the method of embodiment 25, wherein the fragrance vapor is detected by a gas sensor.

Embodiment 27 is the method of any of embodiments 23 to 25, wherein the fragrance vapor is detected by a living being.

Embodiment 28 is the method of any of embodiments 23 to 27, wherein the minimum temperature is between 30 degrees Celsius and 150 degrees Celsius.

Embodiment 29 is the method of any of embodiments 23 to 28, wherein the minimum temperature is between 45 degrees Celsius and 130 degrees Celsius.

Embodiment 30 is the method of any of embodiments 23 to 29, wherein the composition is heated by a heat gun, a lamp, a torch, electrical resistance, heated liquid, exothermic chemical reaction, solar heat, body heat, or a combination thereof.

Embodiment 31 is the method of any of embodiments 23 to 30, wherein the composition is disposed in a blind location.

Embodiment 32 is the method of embodiment 31, wherein the blind location includes within a housing, behind a wall, behind a ceiling, behind a floor, or a combination thereof.

Embodiment 33 is the method of embodiment 31 or embodiment 32, wherein the blind location is behind an opaque material.

Embodiment 34 is the method of embodiment 33, wherein the opaque material includes a film, a sheet, a foam, a nonwoven material, a woven material, or a combination thereof. Embodiment 34 is the method of embodiment 33 or embodiment 34, wherein the opaque material includes concrete, metal, ceramic, drywall, wood, plastic, cloth, or combinations thereof.

Embodiment 35 is the method of any of embodiments 23 to 34, wherein the matrix includes a polymeric material.

Embodiment 36 is the method of any of embodiments 23 to 35, wherein the matrix includes a film, a nonwoven matrix, a woven matrix, a foam, a multilayer construction, a suspension, a gel, or a combination thereof.

Embodiment 37 is the method of any of embodiments 23 to 36, wherein the matrix includes an adhesive.

Embodiment 38 is the method of any of embodiments 23 to 37, wherein the matrix includes a heat-debondable adhesive.

Embodiment 39 is the method of any of embodiments 23 to 38, wherein the polymeric composite particles are not visible from an exterior of the composition.

Embodiment 40 is the method of any of embodiments 23 to 39, wherein the fragrance includes a water soluble fragrance.

Embodiment 41 is the method of any of embodiments 23 to 39, wherein the fragrance includes a water insoluble fragrance.

Embodiment 42 is the method of any of embodiments 23 to 41, wherein the fragrance has a vapor pressure at 25 degrees Celsius of at least 0.05 mmHg.

Embodiment 43 is the method of any of embodiments 23 to 42, wherein the polymeric composite particles further include a coating layer around the porous polymer core, the coating layer including a thermoplastic polymer, a wax, or a mixture thereof.

Embodiment 44 is the method of embodiment 43, wherein the coating layer includes a silicone-based thermoplastic polymer, a (meth)acrylate-based thermoplastic polymer, an olefin-based thermoplastic polymer, a styrene-based thermoplastic polymer, a phenoxy-based resin, polyvinyl pyrrolidone, animal wax, vegetable wax, petroleum wax, hydrogenated vegetable oil, or a combination thereof.

Embodiment 45 is the method of embodiment 43 or embodiment 44, wherein the coating layer includes a linear thermoplastic polymer.

Embodiment 46 is the method of any of embodiments 43 to 45, wherein the coating layer includes high density polyethylene.

Embodiment 47 is the method of any of embodiments 43 to 46, wherein the coating layer has a thickness in a range of 0.1 micrometers to 5 micrometers.

Embodiment 48 is the method of any of embodiments 43 to 47, wherein the polymeric composite particle has a core-shell configuration with the core being the porous polymeric core particle and the shell being the coating layer.

Embodiment 49 is the method of any of embodiments 23 to 46, wherein the polymeric composite particles are present in the matrix in an amount of at least 0.05% by weight of the total composition.

Embodiment 50 is the method of any of embodiments 23 to 49, wherein the polymeric composite particles are present in the matrix in an amount of between 0.05% and 5% by weight of the total composition.

Embodiment 51 is the method of any of embodiments 23 to 50, wherein the polymeric composite particles are present in the matrix in an amount of between 0.1% and 3% by weight of the total composition.

Embodiment 52 is the method of any of embodiments 23 to 51, wherein the polymeric core has an average diameter in a range of 1 to 200 micrometers.

Embodiment 53 is the method of any of embodiments 23 to 52, wherein the polymeric core has pores having an average size in a range of 1 to 200 nanometers.

Embodiment 54 is the method of any of embodiments 23 to 53, wherein the porous polymeric core comprises a polymerized product of a reaction mixture including a) a first phase and b) a second phase dispersed in the first phase. The first phase includes 1) water and a polysaccharide dissolved in the water and/or 2) a surfactant and a compound of Formula (I).

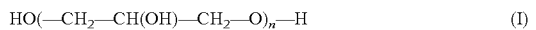

HO(—CH$_2$—CH(OH)—CH$_2$—O)$_n$—H    (I)

In Formula (I), n is an integer equal to at least 1. A volume of the first phase is greater than a volume of the second phase. The second phase includes 1) a monomer composition comprising a monomer of Formula (II) and 2) a poly(propylene glycol) having a weight average molecular weight of at least 500 grams/mole. The poly(propylene glycol) is removed from the polymerized product to provide the porous polymeric core.

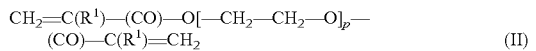

CH$_2$=C(R$^1$)—(CO)—O[—CH$_2$—CH$_2$—O]$_p$—
(CO)—C(R$^1$)=CH$_2$    (II)

In Formula (II), p is an integer equal to at least 1 and R$^1$ is a hydrogen or alkyl.

Embodiment 55 is the method of any of embodiments 23 to 54, wherein the matrix is disposed on one or more electrical wires.

Embodiment 56 is a polymeric composite particle including a) a porous polymeric core; b) a fragrance positioned within the porous polymeric core; and c) a coating layer around the porous polymeric core. The coating layer includes a thermoplastic polymer, a wax, or a mixture thereof. The fragrance is not covalently bonded to the porous polymeric core. The porous polymeric core comprises a polymerized product of a reaction mixture including a) a first phase and b) a second phase dispersed in the first phase. The first phase includes 1) water and a polysaccharide dissolved in the water and/or 2) a surfactant and a compound of Formula (I).

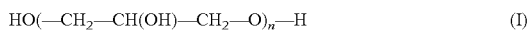

HO(—CH$_2$—CH(OH)—CH$_2$—O)$_n$—H    (I)

In Formula (I), n is an integer equal to at least 1. A volume of the first phase is greater than a volume of the second phase. The second phase includes 1) a monomer composition comprising a monomer of Formula (II) and 2) a poly(propylene glycol) having a weight average molecular weight of at least 500 grams/mole. The poly(propylene glycol) is removed from the polymerized product to provide the porous polymeric core.

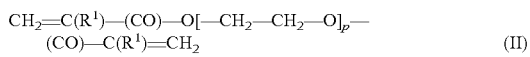

CH$_2$=C(R$^1$)—(CO)—O[—CH$_2$—CH$_2$—O]$_p$—
(CO)—C(R$^1$)=CH$_2$    (II)

In Formula (II), p is an integer equal to at least 1 and R$^1$ is a hydrogen or alkyl.

Embodiment 57 is the polymeric composite particle of embodiment 56, wherein the fragrance includes a water soluble fragrance.

Embodiment 58 is the polymeric composite particle of embodiment 56, wherein the fragrance includes a water insoluble fragrance.

Embodiment 59 is the polymeric composite particle of any of embodiments 56 to 58, wherein the fragrance has a vapor pressure at 25 degrees Celsius of at least 0.05 mmHg.

Embodiment 60 is the polymeric composite particle of any of embodiments 56 to 58, wherein the coating layer includes a silicone-based thermoplastic polymer, a (meth)acrylate-based thermoplastic polymer, an olefin-based thermoplastic polymer, a styrene-based thermoplastic polymer, a phenoxy-based resin, polyvinyl pyrrolidone, animal wax, vegetable wax, petroleum wax, hydrogenated vegetable oil, or a combination thereof.

Embodiment 61 is the polymeric composite particle of any of embodiments 56 to 60, wherein the coating layer includes a linear thermoplastic polymer.

Embodiment 62 is the polymeric composite particle of any of embodiments 56 to 61, wherein the coating layer includes high density polyethylene.

Embodiment 63 is the polymeric composite particle of any of embodiments 56 to 62, wherein the coating layer has a thickness in a range of 0.1 micrometers to 5 micrometers.

Embodiment 64 is the polymeric composite particle of any of embodiments 56 to 58, wherein the polymeric composite particle has a core-shell configuration with the core being the porous polymeric core particle and the shell being the coating layer.

Embodiment 65 is the polymeric composite particle of any of embodiments 56 to 64, wherein the polymeric core has an average diameter in a range of 1 to 200 micrometers.

Embodiment 66 is the polymeric composite particle of any of embodiments 56 to 65, wherein the polymeric core has pores having an average size in a range of 1 to 200 nanometers.

EXAMPLES

Unless otherwise noted, all chemicals used in the examples can be obtained from Sigma-Aldrich Corp. (Saint Louis, Mo.). Unless otherwise specified, all microbiological supplies and reagents were purchased as standard products from either Sigma-Aldrich or VWR.

TABLE 1

Materials

| Designation | Description |
| --- | --- |
| Acrylic Acid | Acrylic monomer from BASF (Ludwigshafen, Germany) |
| APG 325N | Nonionic alkyl polyglucoside surfactant, obtained from Cognis Corporation (Cincinnati, OH, USA) |
| CN2295 | Hexafunctional polyester acrylate oligomer from Sartomer (Exton, PA, USA) |
| CN965 | Aliphatic polyester based urethane diacrylate oligomer from Sartomer (Exton, PA, USA) |
| 2-Ethylhexylacrylate (2-EHA) | Acrylic monomer from BASF (Ludwigshafen, Germany) |
| Glycerol | Obtained from Sigma-Aldrich Corp. (Saint Louis, MO, USA) |
| 2-Hydroxyethylacrylate (HEA) | Acrylic monomer from BASF (Ludwigshafen, Germany) |
| IPA | Isopropyl alcohol, obtained from Sigma Aldrich (St. Louis, MO, USA) |
| IRGACURE 651 | Trade designation for the photoinitiator benzyldimethyl ketal, obtained from BASF (Ludwigshafen, Germany) |
| IRGACURE 819 | Trade designation for the photoinitiator bis(2,4,6-trimethylbenzoyl)-phenylphosphineooxide, obtained from BASF (Florham Park, NJ, USA) |
| Iso-Bornyl Acrylate | Acrylic monomer from San Esters (New York, NY, USA) |
| Mowital B60H (PVB) | Polyvinyl butyral obtained from Kuraray (Tokyo, Japan) |
| PPG4000 | Polypropylene glycol having a weight average molecular weight of 4000 grams/mole, obtained from Alfa Aesar (Ward Hill, MA, USA) |
| PVP | Polyvinylpyrrolidone, obtained from Polysciences, Inc. (Warrington, PA, USA) |
| Shrink Box 1525 | Polyolefin-based shrink film, obtained from Clysar LLC (Clinton, IA, USA) |
| 2-Sulfoethyl Methacrylate | Monomer available from Scientific Polymer, Inc. (Ontario, NY, USA) |
| SR 339 | Trade designation for 2-phenoxyethyl acrylate ester obtained from Sartomer Company, Inc. (Exton, PA, USA) |
| SR 6030P | Trade designation for polyethylene glycol 400 dimethacrylate with a weight average molecular weight of 400 grams/mole obtained from Sartomer Company, Inc. (Exton, PA, USA) |
| Tape Primer 94 | Adhesion promoter for various surfaces, obtained from 3M Company (St. Paul, MN, USA) |
| VHB 5925P Tape | 25 mil (0.635 mm) thick, closed cell pressure sensitive, acrylic foam tape, obtained from 3M Company (St. Paul, MN, USA) |

Test Methods:
Thermogravimetric Analysis

Thermogravimetric analysis (TGA) was performed on a TA Instruments Inc. (New Castle, Del.) Q500 model. Testing was done in standard aluminum pans at a rate of 10° C./min from 35° C. to 500° C. The data from the ramping heat process was graphed on a chart showing mass loss (%) versus temperature (° C.).

Preparative Example 1 (PE-1): Synthesis of Nanoporous Microparticles Having Hydrophobic and Hydrophilic Moieties The monomers SR 339 (50 grams), SR 6030P (50 grams), and sulfoethyl methacrylate (5 grams) were mixed with PPG4000 (43 grams) and IRGACURE 819 (250 milligrams). The mixture was stirred vigorously for 20 minutes on gentle heat of about 40° C. to 50° C. The mixture was then added to 250 grams of glycerol previously mixed with the 7.5 grams of the surfactant APG 325N. The mixture was shear mixed for 20 minutes. The mixture was then spread thin between two sheets of polyethylene terephthalate (PET) and cured with ultraviolet light for 10 to 15 minutes with a 100 Watts, long-wavelength BLACK RAY UV lamp (obtained from UVP, LLC of Upland, Calif., USA) situated at about 15 centimeters (6 inches) from the surface of the curing material.

Figure 8A:
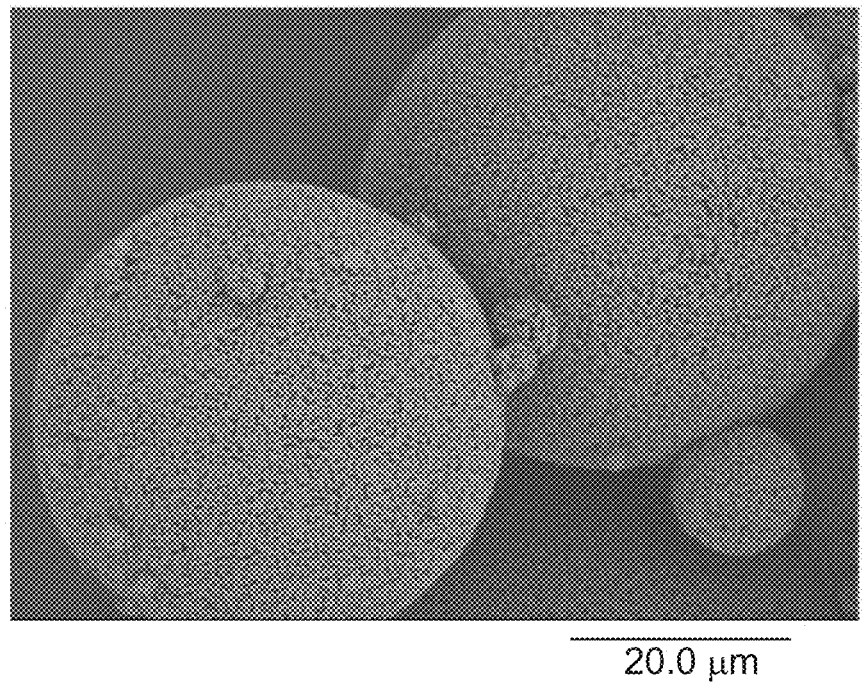
FIG. 8A is the scanning electron micrograph (SEM) of porous polymeric particles prepared as described in Preparatory Example 1.
Figure 8B:
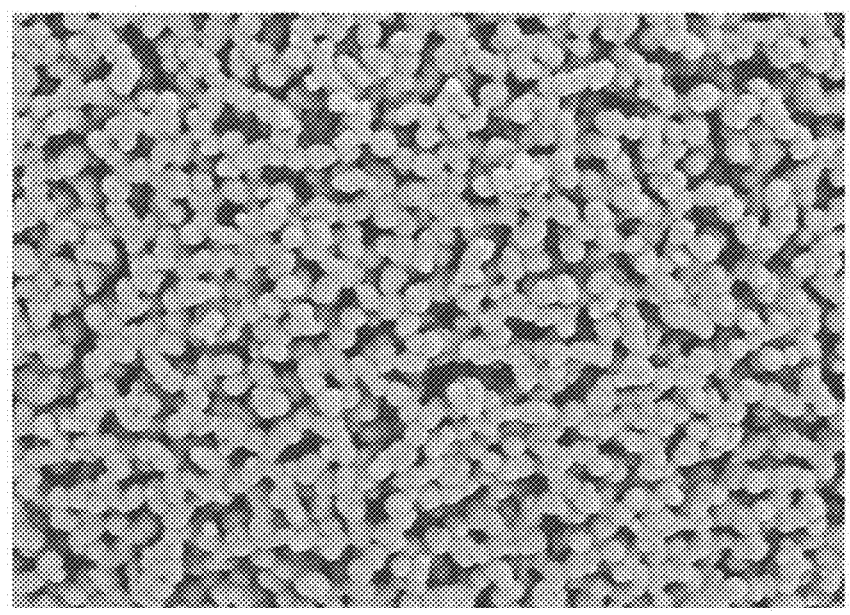
FIG. 8B is the SEM of a porous polymeric particle of FIG. 8A at a higher resolution.

The cured mixture was then dispersed in excess water (500 mL), shaken for 30 minutes, and centrifuged at 3000 rpm in an EPPENDORF 5810 R centrifuge (obtained from Eppendorf in Germany). The supernatant was removed and the resulting particles were then re-suspended in 500 mL of water for a second rinse followed by centrifugation. After this, the particles were suspended in a 500 mL isopropyl alcohol and shaken for 20 minutes. This extracted the PPG and left voids (i.e., pores or free volume) in the particles. The particles were then centrifuged at 300 rpm for 30 minutes and the supernatant was discarded. The particles were oven-dried overnight at 70° C. to eliminate any isopropyl alcohol left in the mixture. FIG. 8A is a digital SEM image of the particles from PE-1. FIG. 8B is a digital SEM image of the particles from PE-1 at a higher magnification.

Preparative Example 2 (PE-2): Preparation of Polymer Composite Particles Containing Menthol After the particles of PE-1 were synthesized and characterized by SEM, 50 grams of dry particles were filled with a solution of 10.0 grams menthol dissolved into 50 grams of dichloromethane. The particles were air dried overnight and then vacuum dried for 1 hour. Next, the particles were added to 375 grams of distilled water and 132 grams of polyvinylpyrrollidone (10 kDa) and further mixed with an ultrasonic probe. This polymer mixture was then used as the precursor slurry for spray drying to microencapsulate the particles by coating a 1 micrometer polymer shell around the menthol containing particles.

Figure 9B:
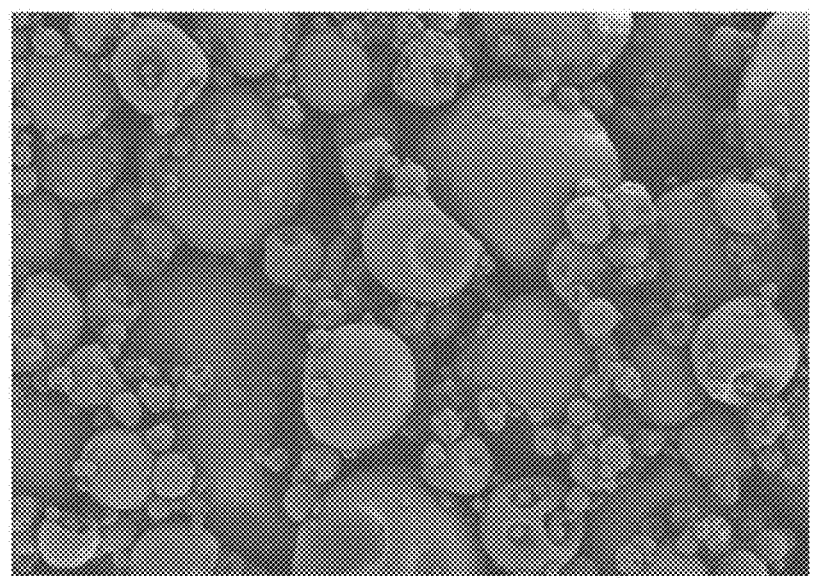
FIG. 9B is the SEM of a polymeric composite particle of FIG. 9A at a higher resolution.

The slurry created as outlined above was dried with a customized MODEL 48 mixed flow spray dryer fabricated by Spray Drying Systems, Inc. (headquartered in Eldersburg, Md.). The spray dryer is 4 feet (1.2 meters) in diameter and has 8 foot (2.4 meters) straight sides. The spray dryer was operated in closed loop mode (the system is purged with nitrogen, which is then recycled during operation as the bulk drying gas). During operation this bulk drying gas was heated via an electric heater and carried through the drying chamber (entered through the top and exited through the bottom) and finally to a cyclone and a baghouse before passing through the blower and the condenser (to condense out the solvent) before returning to the heater for reuse. The bulk drying gas temperature at the chamber inlet was 91-96° C., and at the outlet was 56° C. The slurry was provided at 20-40 grams/minute via a peristaltic pump. The slurry was atomized vertically upward utilizing internally mixed two-fluid pressure spray atomizing nozzles (available from Spraying Systems Co. (Wheaton, Ill.) under the trade designations "FLUID CAP 100150" and "AIR CAP 170"). The atomizing gas was nitrogen, provided at 25 psi (0.17 MPa) and 1.65 (±0.05) standard cubic feet per minute (~46.7 standard liters per minute). FIG. 9A is a digital SEM image of the polymer composite particles from PE-2. FIG. 9B is a digital SEM image of the polymer composite particles from PE-2 at a higher magnification.

Preparative Example 3 (PE-3): Preparation of Polymer Composite Particles Containing Ethyl Butyrate Another batch of particles was synthesized using the same procedure as described in PE-1. Then, 40 grams of dry particles were infused with 40 grams of ethyl butyrate. The particles were dried with an IR lamp overnight. Next, the mixture of particles and ethyl butyrate were added to 600 mL of distilled water and 212 grams of polyvinylpyrrolidone and further mixed with a high shear blender. This polymer mixture was then used to coat a 1 micrometer polymer shell around the particles via spray drying. The slurry was spray dried as in PE-2, with Fluid Cap 60100 and Air Cap 120. The inlet drying gas temperature was 88-107° C. and the outlet temperature was 60° C. Atomizing nitrogen was provided at 3.45 (±0.05) standard cubic feet per minute and at 12.5 psi and the slurry was provided at 20 (±5) grams/minute.

Example 1 (EX-1): Release of Menthol from Polymer Composite Particles

Figure 12:
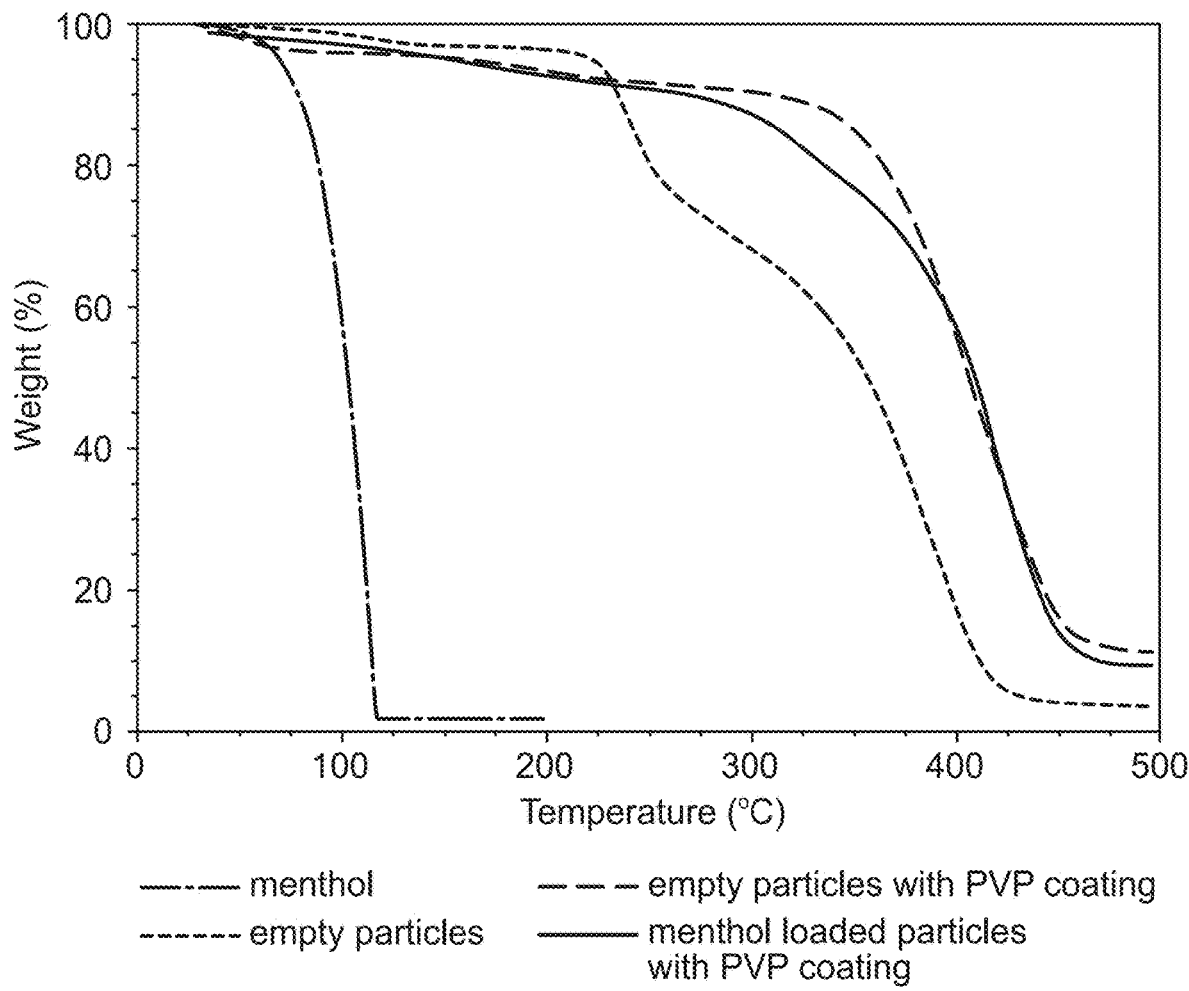
FIG. 12 is a plot of the thermogravimetric analysis test results of polymeric composite particles containing menthol.

Thermogravimetric analysis (TGA) was performed on polymer composite particles loaded with menthol. The mass loss behavior indicates the various steps in the process of fragrance release and material decomposition. The first occurrence of mass loss in the menthol-loaded particles began around 50° C., which indicated the loss of moisture in the sample. The second phase of mass loss in the menthol-loaded particles began around 120° C., indicating the triggered release of the menthol fragrance. The last phase of mass loss in the menthol-loaded particles began around 300° C., indicating the particle material decomposition. The mass loss profile for the non-loaded, PVP coated particles was very similar to that of the menthol-loaded one. One observable difference between the two profiles was that the non-loaded particles had less mass loss following the triggered release point than the menthol-loaded particles, which was because the particles were empty. The non-loaded particles also retained their mass to higher temperatures before their eventual decomposition. The mass loss profile of menthol exhibited the sublimation of menthol, which began around 55° C. FIG. 12 shows the TGA plot of mass loss versus temperature for menthol, empty porous polymeric particles, empty porous polymeric particles coated with PVP, and menthol loaded porous polymeric particles coated with PVP.

Head space gas chromatography was performed on an Agilent Technologies G1888 Headspace Autosampler (Santa Clara, Calif.). For testing of the polymer composite particles containing menthol and menthol control samples, an aliquot of 2 milligrams of each sample were weighed into tared headspace sample vials. The vials were then sealed with a Teflon lined septa and analyzed by headspace GC/MS. The samples were heated to a specified temperature and then the headspace of the sample was analyzed. The following analytical conditions were used:
Headspace Sampler Conditions:
Sample oven temperature: 90° C., 100° C., 110° C., 120° C., 130° C., 140° C., 150° C., 160° C., 170° C.
Sample loop temperature: 100° C., 120° C., 180° C.
Transfer line temperature: 180° C.
GC cycle time: 20 minutes
Sample equilibration time: 10 minutes
Vial pressurization: 1.0 minute at 16 psi (110.3 kilopascals)
Loop fill time: 0.5 minutes
Loop equilibration time: 0.1 minutes
Sample inject time: 1.0 minute
GC/MS Conditions:
Instrument: HP 6890 GC+5973 MSD
Column: Agilent DB-5 30m×0.32 mm ID, 1 µm film
Carrier: Helium at 2.0 mL/min. constant flow mode;
Inlet: split injection, 10/1 split ratio: [180° C.]
Oven: 50° C. [1 min] @ 20° C./min to 320° C., [3 min]
Detection: EI mass spec at 70 eV, Scan mode, 29 to 550 Da.
Aux 280° C.

Figure 13:
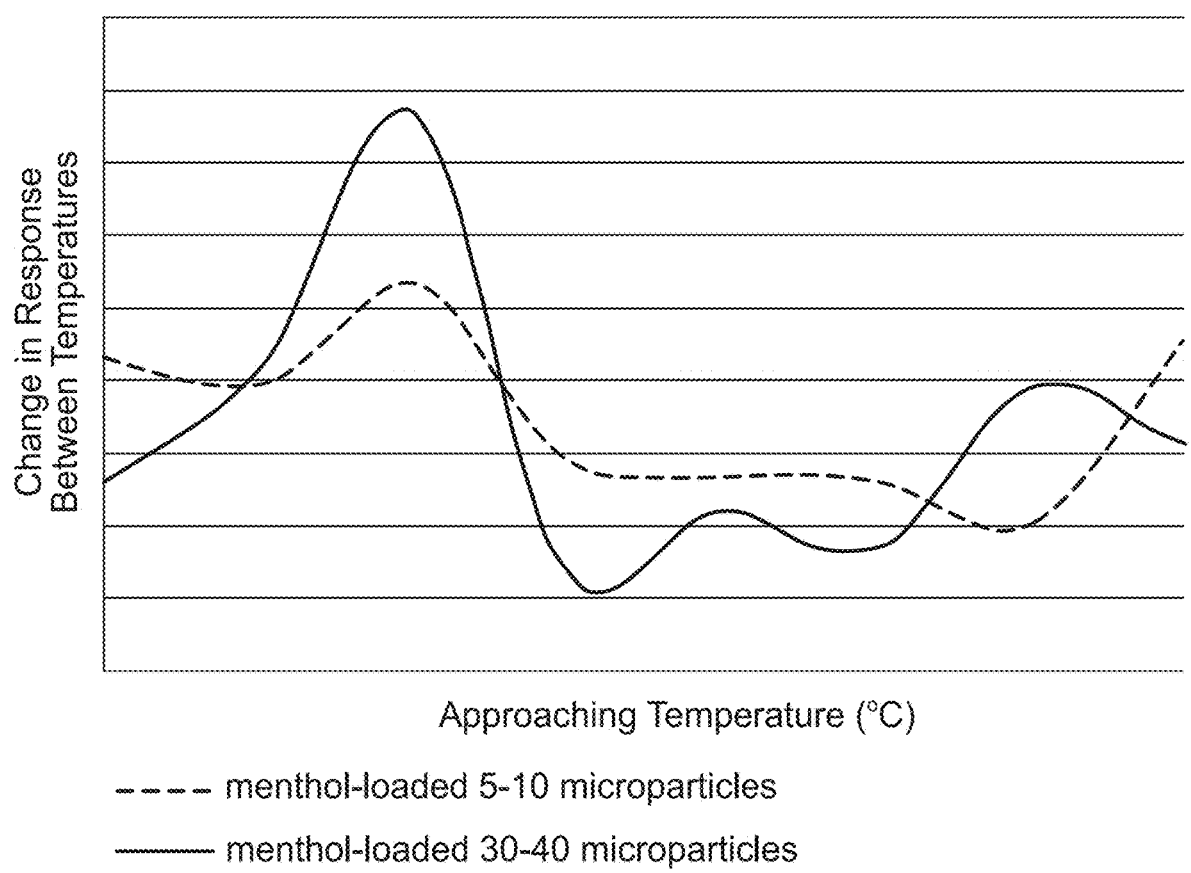
FIG. 13 is a plot of the change in menthol detected by gas chromatography at different temperatures from different sized polymeric composite particles containing menthol.

Table 2 shows the controlled release of the menthol-loaded microparticles compared to the menthol control. FIG. 12 shows that the greatest increase in menthol being detected occurs at 120° C., which is the microparticles triggered release point. Increasing the temperature from the trigger point showed minimal to no improvement in menthol being detected. FIG. 13 illustrates the differences in menthol detected by gas chromatography between 5-10 micrometer diameter particles and 30-40 micrometer diameter particles.

TABLE 2

Menthol detected by head space gas chromatography.

| | Response Per Milligram of Menthol Content ($\times 10^{11}$) | | |
|---|---|---|---|
| Temperature (° C.) | Menthol Control | 5-10 µm Polymeric Composite Particles | 30-40 µm Polymeric Composite Particles |
| 90 | 7.25 | 1.75 | 2.12 |
| 100 | 16.85 | 1.98 | 2.18 |
| 110 | 17.59 | 2.17 | 2.40 |
| 120 | 23.93 | 2.51 | 2.97 |
| 130 | 23.97 | 2.60 | 2.90 |
| 140 | 25.68 | 2.67 | 2.92 |
| 150 | 24.64 | 2.73 | 2.89 |
| 160 | 25.01 | 2.73 | 3.08 |
| 170 | 30.45 | 2.98 | 3.19 |

Example 2 (EX-2): Release of Ethyl Butyrate from Polymer Composite Particles

Figure 14:
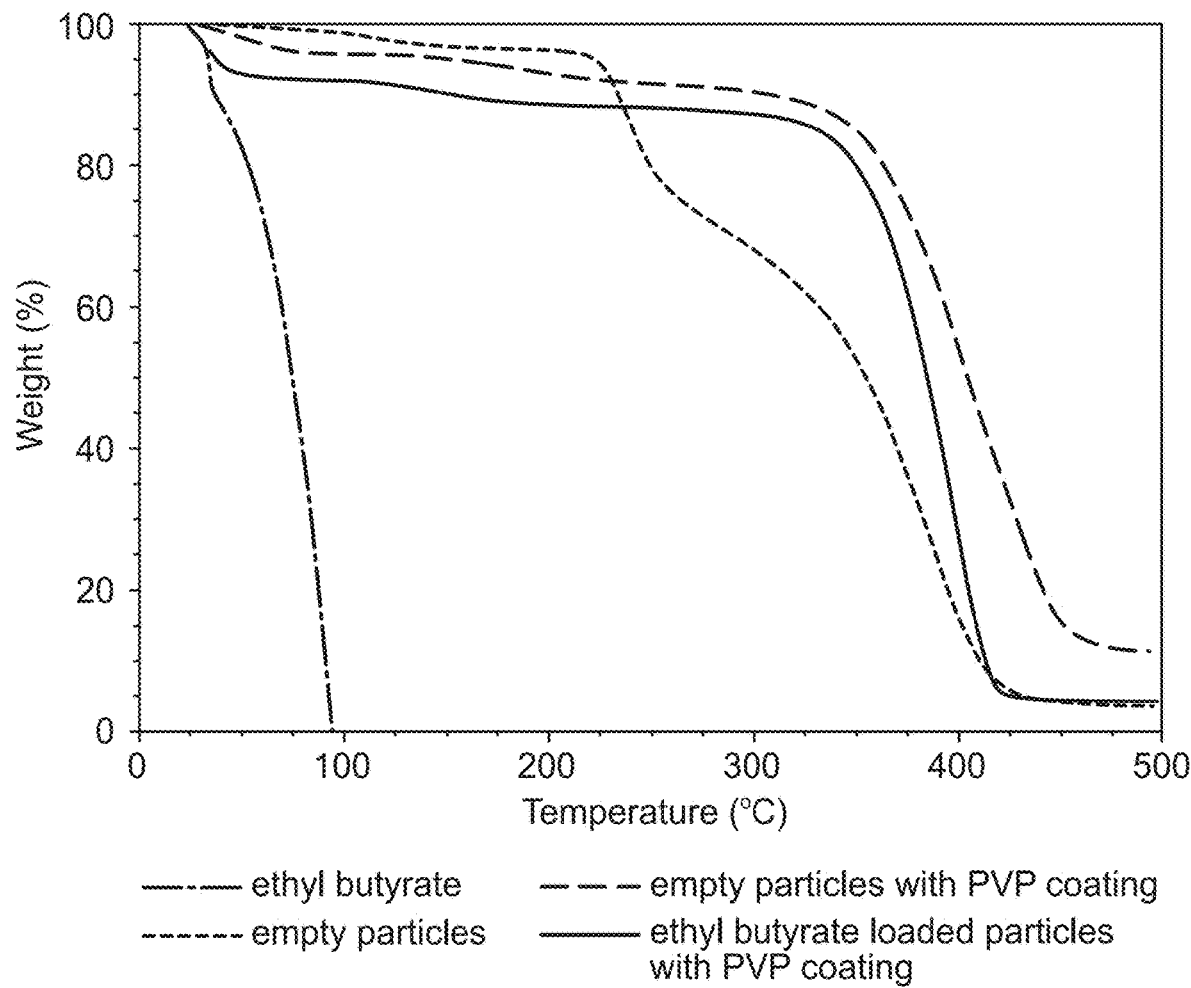
FIG. 14 is a plot of the thermogravimetric analysis test results of polymeric composite particles containing ethyl butyrate.

Thermogravimetric analysis (TGA) was performed on polymer composite particles loaded with menthol. The mass loss behavior indicates the various steps in the process of fragrance release and material decomposition. The first occurrence of mass loss in the ethyl butyrate-loaded particles began almost immediately, which indicated the loss of moisture in the sample. The second phase of mass loss in the ethyl butyrate-loaded particles began around 125° C., indicating the triggered release of the ethyl butyrate fragrance. The last phase of mass loss in the ethyl butyrate loaded-particles began around 300° C., indicating the particle material decomposition. The mass loss profile for the non-loaded, PVP coated particles was very similar to that of the ethyl butyrate-loaded one. One observable difference between the two profiles was that the non-loaded particles had less mass loss following the triggered release point than the ethyl butyrate-loaded particles, which was because the particles were empty. The non-loaded particles also retained their mass to higher temperatures before their eventual decomposition. The mass loss profile of ethyl butyrate exhibited the evaporation of ethyl butyrate due to its vapor pressure, which began at the start of the test. FIG. 14 shows the TGA plot of mass loss versus temperature for ethyl butyrate, empty porous polymeric particles, empty porous polymeric particles coated with PVP, and ethyl butyrate loaded porous polymeric particles coated with PVP.

Head space gas chromatography was performed on an Agilent Technologies G1888 Headspace Autosampler (Santa Clara, Calif.). For testing of the polymer composite particles containing ethyl butyrate and ethyl butyrate control samples, an aliquot of 5 milligrams of the particles or 1.5 milligrams of the ethyl butyrate were weighed into tared headspace sample vials. The vials were then sealed with a Teflon lined septa and analyzed by headspace GC/MS. The samples were heated to a specified temperature and then the headspace of the sample was analyzed. The following analytical conditions were used:
Headspace Sampler Conditions:
Sample oven temperature: 90° C., 100° C., 110° C., 120° C., 130° C., 140° C., 150° C., 160° C., 170° C.
Sample loop temperature: 90° C., 120° C., 150° C., 180° C.
Transfer line temperature: 180° C.
GC cycle time: 20 minutes
Sample equilibration time: 10 minutes
Vial pressurization: 1.0 minute at 16 psi (110.3 kilopascals)
Loop fill time: 0.5 minutes
Loop equilibration time: 0.1 minutes
Sample inject time: 1.0 minute
   GC/MS Conditions:
Instrument: HP 6890 GC+5973 MSD
Column: Agilent DB-5 30m×0.32 mm ID, 1 μm film
Carrier: Helium at 2.0 mL/min. constant flow mode;
Inlet: split injection, 10/1 split ratio: [180° C.]
Oven: 50° C. [1 min] @ 20° C./min to 320° C., [3 min]
Detection: EI mass spec at 70 eV, Scan mode, 29 to 550 Da.
Aux 280° C.

Table 3 shows the controlled release of the ethyl butyrate-loaded microparticles compared to the ethyl butyrate control.

TABLE 3

Ethyl butyrate detected by head space gas chromatography.

| Temperature (° C.) | Response Per Milligram of Ethyl Butyrate Content (×10$^5$) | |
| --- | --- | --- |
| | Ethyl Butyrate Control | Polymeric Composite Particles |
| 90 | 234.67 | 3.99 |
| 100 | 280.72 | 4.10 |
| 110 | 260.51 | 4.88 |
| 120 | 258.65 | 6.66 |
| 130 | 291.05 | 8.15 |
| 140 | 287.39 | 10.69 |
| 150 | 270.84 | 14.53 |
| 160 | 275.40 | 18.21 |
| 170 | 271.79 | 22.90 |

Example 3 (EX-3): VHB Tape Sample

A 1 inch×1 inch (2.54 cm×2.54 cm) strip of VHB 5925P Tape (obtained from 3M Company, St. Paul, Minn.), was cut and 10 milligrams of the menthol loaded microparticles were evenly sprinkled onto the exposed adhesive side of the tape. Next, a 1 inch×1 inch (2.54 cm×2.54 cm) piece of Shrink Box 1525 shrink film (obtained from Clysar LLC, Clinton, Iowa), primed with Tape Primer 94 and laminated with a 2 mil (0.05 mm) acrylic transfer tape was cut. The shrink film side was laminated to the exposed adhesive side of the VHB tape. The two films were pressed together by passing a 4.5 pound (2 kg) roller over them six times.
Testing
The VHB tape sample was added to a vial. The vial was then sealed with a Teflon lined septa and analyzed by headspace GC/MS.

Example 4 (EX-4): Wire Coating Sample

A 1 inch×¾ inch (2.54 cm×1.91 cm) strip of Super 33+ Vinyl Electrical Tape (obtained from 3M Company, St. Paul, Minn.), was cut and 5 milligrams of the menthol loaded microparticles were evenly sprinkled onto it. Next, a 1 in (2.54 cm) long segment of a steel wire hanger was cut. The piece of electrical tape with the microparticles on it was then wrapped around the piece of steel wire to create a wire coating.
Testing
The coated wire sample was added to a vial. The vial was then sealed with a Teflon lined septa and analyzed by headspace GC/MS.

Example 5 (EX-5): Sponge Sample

A 1 inch×1 inch (2.54 cm×2.54 cm) piece of an O-CELLO medium sponge (obtained from 3M Company, St. Paul, Minn.), was cut out and allowed to dry out overnight. After drying, the piece of sponge was sprayed with SCOTCH Photo Mount Adhesive Spray (obtained from 3M Company, St. Paul, Minn.), to apply a layer of adhesive to it. After being sprayed with adhesive, the sponge was allowed to dry again for 5 minutes. Then 15 milligrams of menthol loaded microparticles were evenly sprinkled onto the adhesive sprayed side of the sponge.
Testing
The sponge sample was added to a vial. The vial was then sealed with a Teflon lined septa and analyzed by headspace GC/MS.

Example 6 (EX-6): Nonwoven Sample

A 1 inch×1 inch (2.54 cm×2.54 cm) piece of a SCOTCH-BRITE nonwoven scour pad (obtained from 3M Company, St. Paul, Minn.), was cut out and sprayed with SCOTCH Photo Mount Adhesive Spray (obtained from 3M Company, St. Paul, Minn.), to apply a layer of adhesive to it. After being sprayed with adhesive, the scour pad was allowed to dry again for 5 minutes. Then 15 milligrams of menthol loaded microparticles were evenly sprinkled onto the adhesive sprayed side of the sponge.

Testing

The nonwoven sample was added to a vial. The vial was then sealed with a Teflon lined septa and analyzed by headspace GC/MS.

Example 7 (EX-7): Film Sample

The following table is a breakdown of each component needed to make 3 kg of acrylic film syrup on a weight percent (wt %) basis.

TABLE 4

List of components and their required amounts of wt % basis

| Components: | 2-EHA | IBOA | PVB | AA | HEA | CN965 | CN2295 | IRG 651 |
|---|---|---|---|---|---|---|---|---|
| Amount (wt %): | 26.80% | 23.89% | 18.79% | 11.17% | 11.17% | 7.82% | 0.15% | 0.22% |
| Amount (g): | 804 | 716.7 | 563.7 | 335.1 | 335.1 | 234.6 | 4.5 | 6.6 |

In a one gallon jar all of the components with their respective amounts were added and then mixed together using a multispeed homogenizer model MUD1001AN by Carter Motor Company (Warren, Ill., USA) with a 1.5 inch (3.81 cm) diameter Cowles blade at 3500 rpm for 10 minutes so that the mixture was uniform. 15 grams of the acrylic syrup were then added to a FlackTek Max 20 speed mixing jar (Landrum, S.C.) along with 150 milligrams of the menthol loaded microparticles. The mixture was then mixed using a FlackTek Inc. SpeedMixer model DAC 150FV (Landrum, S.C.) at 2000 rpm for 1 minute. After mixing, the jar was degassed at −20 inches of Hg for 10 minutes. The film was then constructed by coating a 4 mil (0.10 mm) thick layer of the mixture using a notch bar coater. It was then cured by photopolymerizing it using UV lights at an intensity of 12 mW/cm$^2$ for 228 seconds.

Testing

The film sample was added to a vial. The vial was then sealed with a Teflon lined septa and analyzed by headspace GC/MS.

Example 8 (EX-8): Mineral Oil Sample

In a FlackTek Max 20 speed mixing jar (Landrum, S.C.), 10 grams of Swan Mineral Oil U.S.P. (obtained from Vi-Jon, St. Louis, Mo.) were added along with 100 milligrams of menthol loaded microparticles. The mixture was then mixed using a FlackTek Inc. SpeedMixer Model DAC 150FV (Landrum, S.C.) at 2000 rpm for 1 minute.

Testing 100 milligrams of the mineral oil and menthol loaded microparticles mixture was added to a vial. The vial was then sealed with a Teflon lined septa and analyzed by headspace GC/MS.

Head Space Chromatography Testing Conditions

All samples for Examples 3-8 were heated to a specified temperature and then the headspace of the samples was analyzed. The following analytical conditions were used:

Headspace Sample Conditions:
Instrument: Agilent Technologies G1888 headspace autosampler
Sample oven temperature: 40° C., 80° C., 90° C., 100° C., 110° C., 120° C., 130° C., 140° C., 150° C.
Sample loop temperature: 80° C., 150° C.
Transfer line temperature: 180° C.
GC cycle time: 25 min.
Sample equilibration time: 25 min
Vial pressurization: 1.0 min. at 16 psi (110.3 kilopascals)
Loop fill time: 0.5 min.
Loop equilibration time: 0.1 min.
Sample inject time: 1.0 min.

GC/MS Conditions:
Instrument: HP 6890 GC+5973 MSD
Column: Agilent DB-5 30m×0.32 mm ID, 1 μm film
Carrier: Helium at 2.0 mL/min. constant flow mode;
Inlet: split injection, 10/1 split ratio: [180° C.]
Oven: 50° C. [1 min] @ 20° C./min to 320° C., [3 min]
Detection: EI mass spec at 70 eV, Scan mode, 29 to 550 Da. Aux 280° C.

TABLE 5

Menthol detected by head space gas chromatography.
Normalized Results for Menthol (×10$^5$)

| Temperature (° C.) | Wire | VHB | Scour Pad | Sponge | Film | Mineral Oil |
|---|---|---|---|---|---|---|
| 40 | 0 | 0 | 0 | 0 | 1.13 | 1.74 |
| 80 | 12.67 | 4.78 | 10.58 | 34.45 | 8.98 | 17.94 |
| 90 | 29.53 | 9.52 | 22.79 | 59.28 | 20.29 | 13.67 |
| 100 | 56.10 | 27.65 | 40.26 | 92.91 | 34.83 | 22.48 |
| 110 | 100.31 | 47.59 | 67.59 | 156.98 | 82.06 | 52.35 |
| 120 | 153.55 | 68.03 | 114.77 | 243.72 | 106.93 | 79.30 |
| 130 | 295.45 | 112.84 | 138.12 | 288.28 | 167.35 | 153.11 |
| 140 | 421.51 | 135.48 | 137.09 | 266.43 | 240.10 | 159.19 |
| 150 | 550.95 | 193.78 | 197.35 | 516.41 | 326.73 | 193.65 |

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. Furthermore, all publications, published patent applications and issued patents referenced herein are incorporated by reference in their entirety to the same extent as if each individual publication or patent was specifically and individually indicated to be incorporated by reference. Various exemplary embodiments have been described. These and other embodiments are within the scope of the following listing of disclosed embodiments.

What is claimed is:

1. A method of determining a minimum temperature of a composition comprising:
   a) providing a composition comprising a plurality of polymeric composite particles disposed in a matrix, wherein the polymeric composite particles comprise a porous polymeric core, a fragrance positioned within the porous polymeric core, and a coating layer around the porous polymeric core, wherein the coating layer covers the entire exterior surface of the polymeric composite particle and wherein the coating layer comprises a thermoplastic polymer, a wax, or a mixture thereof;
   b) heating the composition;
   c) releasing at least a portion of the fragrance as a vapor from the porous polymeric core of the polymeric composite particles at or above the minimum temperature; and
   d) detecting at least a portion of the fragrance vapor in a location outside of the matrix.

2. The method of claim 1, wherein the fragrance vapor is detected at a concentration of at least 0.5 parts per billion.

3. The method of claim 1, wherein the fragrance vapor is detected at a concentration of at least 1 part per million.

4. The method of claim 1, wherein the fragrance vapor is detected by a gas sensor.

5. The method of claim 1, wherein the minimum temperature is between 30 degrees Celsius and 150 degrees Celsius.

6. The method of claim 1, wherein the composition is heated by a heat gun, a lamp, a torch, electrical resistance, heated liquid, exothermic chemical reaction, solar heat, body heat, or a combination thereof.

7. The method of claim 1, wherein the composition is disposed in a blind location.

8. The method of claim 1, wherein the blind location comprises within a housing, behind a wall, behind a ceiling, behind a floor, or a combination thereof.

9. The method of claim 8, wherein the blind location is behind an opaque material.

10. The method of claim 9, wherein the opaque material comprises a film, a sheet, a foam, a nonwoven material, a woven material, or a combination thereof.

11. The method of claim 9, wherein the opaque material comprises concrete, metal, ceramic, drywall, wood, plastic, cloth, or combinations thereof.

12. The method of claim 1, wherein the matrix comprises a film, a nonwoven matrix, a woven matrix, a foam, a multilayer construction, a suspension, a gel, or a combination thereof.

13. The method of claim 1, wherein the matrix comprises a heat debondable adhesive.

14. The method of claim 1, wherein the fragrance has a vapor pressure at 25 degrees Celsius of at least 0.05 mmHg.

15. The method of claim 1, wherein the coating layer comprises a silicone-based thermoplastic polymer, a (meth)acrylate-based thermoplastic polymer, an olefin-based thermoplastic polymer, a styrene-based thermoplastic polymer, a phenoxy-based resin, polyvinyl pyrrolidone, animal wax, vegetable wax, petroleum wax, hydrogenated vegetable oil, or a combination thereof.

16. The method of claim 1, wherein the coating layer comprises a linear thermoplastic polymer.

17. The method of claim 1, wherein the coating layer comprises high density polyethylene.

18. The method of claim 1, wherein the coating layer has a thickness in a range of 0.1 micrometers to 5 micrometers.

19. The method of claim 1, wherein the matrix is disposed on one or more electrical wires.

20. The method of claim 1, wherein the porous polymeric core comprises a polymerized product of a reaction mixture comprising:
   i) a first phase comprising a surfactant and a compound of Formula (I)

$$HO-(-CH_2-CH(OH)-CH_2-O)_n-H \qquad (I)$$

wherein n is an integer equal to at least 1, or a mixture thereof; and
   ii) a second phase dispersed in the first phase, wherein a volume of the first phase is greater than a volume of the second phase and wherein the second phase comprises
      1) a first monomer composition comprising a monomer of Formula (II)

$$CH_2=C(R^1)-(CO)-O[-CH_2-CH_2-O]_p-(CO)-C(R^1)=CH_2 \qquad (II)$$

wherein
         p is an integer equal to at least 1;
         $R^1$ is hydrogen or alkyl; and
      2) a poly(propylene glycol) having a weight average molecular weight of at least 500 grams/mole,
   wherein the poly(propylene glycol) is removed from the polymerized product to provide the porous polymeric core.

* * * * *